United States Patent [19]

Arai et al.

[11] Patent Number: 5,530,146
[45] Date of Patent: Jun. 25, 1996

[54] FUROBENZOPYRAN DERIVATIVES, PROCESS FOR PREPARATION OF SAME AND HERBICIDES CONTAINING SAME AS ACTIVE COMPONENTS

[75] Inventors: Kiyoshi Arai; Masayuki Ooka; Fumiaki Koizumi; Sadafumi Koda; Yasunaga Iwasaki; Yoshiro Kanemoto, all of Mobara, Japan

[73] Assignee: Mitsui Toatsu Chemicals, Incorporated, Tokyo, Japan

[21] Appl. No.: 263,824

[22] Filed: Jun. 22, 1994

Related U.S. Application Data

[62] Division of Ser. No. 65,495, May 24, 1993, Pat. No. 5,356,866.

[30] Foreign Application Priority Data

May 28, 1992 [JP] Japan ..................................... 4-136801
Mar. 8, 1993 [JP] Japan ..................................... 5-046218

[51] Int. Cl.⁶ .................................................. C07D 307/20
[52] U.S. Cl. ........................................... 549/476; 549/478
[58] Field of Search ....................................... 549/476, 478

[56] References Cited

PUBLICATIONS

Martin et al., Carbohydrate Research, 171, 211–222 (1987).
Martin et al., ibid., 196, 41–58 (1990).

*Primary Examiner*—Nicky Chan
*Attorney, Agent, or Firm*—Oblon, Spivak, McClelland, Maier, & Neustadt

[57] ABSTRACT

Furobenzopyran derivatives of the general formula (I):

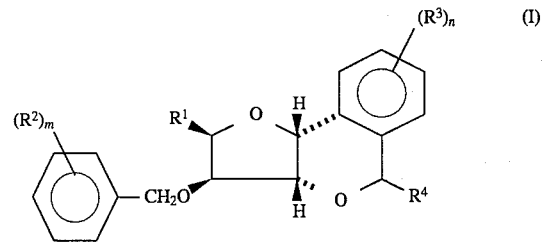

in which $R^1$ is a lower alkyl group, $R^2$ is a lower alkyl group, lower alkoxy group, halogen atom or lower alkyl group substituted by a halogen atom, $R^3$ is a lower alkyl group, lower alkoxy group, halogen atom, lower alkyl group substituted by a halogen atom, phenoxy group or benzyloxy group, $R^4$ is a hydrogen atom or lower alkyl group and m and n are any integers between 0 and 4, have an excellent herbicidal activity on weeds and are completely selective to crops such as paddy rice, soybeans and cotton.

3 Claims, No Drawings

FUROBENZOPYRAN DERIVATIVES, PROCESS FOR PREPARATION OF SAME AND HERBICIDES CONTAINING SAME AS ACTIVE COMPONENTS

This is a division of application Ser. No. 08/065,495, filed on May 24, 1993, now U.S. Pat. No. 5,356,866.

BACKGROUND OF THE INVENTION

1. Field of the Invention

The present invention relates to furobenzopyran derivatives, a process for their preparation and herbicides containing these compounds as active components.

2. Description of Prior Art

Reports on the synthesis of compounds having a furobenzopyran ring are very few, and there are no reports of such compounds exhibiting herbicidal activity. Only one furobenzopyran derivative that reportedly exhibits a biological activity is monocerin of the following formula:

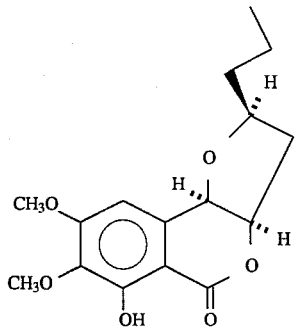

This compound was first reported in J. Chem. Soc. (C) 2598 (1970) as an antifungal metabolite of *Helminthosporium monoceras*. Furthermore, this compound is described in U.S. Pat. No. 3,661,935 as an antifungal compound.

O. R. Martin et al. have described a group of compounds of the following formula in Carbohydr. Res., 196, 41–58 (1990):

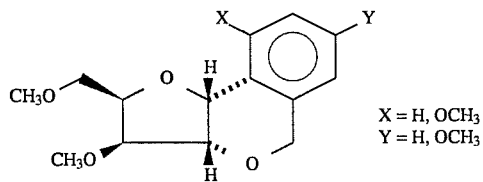

$X = H, OCH_3$
$Y = H, OCH_3$

Further, O. R. Martin has described compounds of the following formulae in Carbohydr. Res., 171, 211–222 (1987):

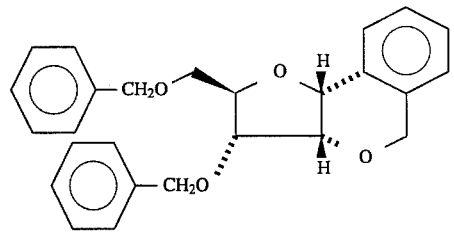

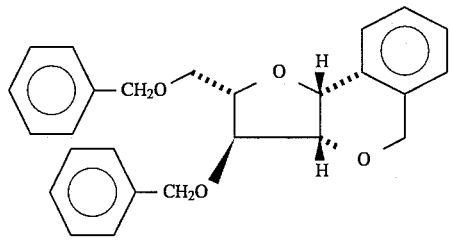

However, there was no statement as to whether these compounds exhibit herbicidal activity or any other biological activities.

To date, a number of herbicides for use in upland fields and rice paddies have been developed, but none of these is satisfactory in terms of herbicidal activity or herbicidal selectivity in crop farming.

SUMMARY OF THE INVENTION

An object of the present invention is to find effective compounds which do not damage cultivated crops under any conditions but selectively exhibit herbicidal activity when used in upland fields as well as rice paddies.

Thus, one aspect of the present invention is to find compounds having excellent potential as herbicides for use in rice paddies, which are sufficiently selective to paddy rice but exhibit a high herbicidal activity on annual weeds such as Echinochloa sp., *Cyperus difformis* L, *Monochoria vaginalis* and *Rotala indica* and perennial weeds such as *Scirpus juncoides*.

Further, another aspect of the present invention is to find compounds which are effective not only as herbicides in rice paddies but also as herbicides in upland fields as well as in other non-agricultural fields by soil application or by foliar application, and thus effective on *Digitaria adscendens*, *Stellaria media*, Persicaria, *Amaranthus retroflexus*, *Cyperus iria*, *Poltulaca oleracea*, *Senecio vulgaris*, *Chenopodium album*, *Cyperus rotundus*, *Calystegia japonica*, *Sagina japonica*, *Galium aparine*, *Alopecurus aequalis*, *Poa annua*, *Capsella bursa pastoris*, *Setaria viridis*, etc.

In order no achieve the above-mentioned objectives, the present inventors studied the herbicidal activity of existing furobenzopyran compounds, and conducted that none of them satisfied the above objectives. Subsequently, the present inventors synthesized a number of novel furobenzopyran compounds and studied their herbicidal activities in various ways. As a result, the present inventors have found compounds which are effective not only as herbicides in rice paddies but also as herbicides in upland fields as well as in other non-agricultural fields, thereby having completed the present invention.

Namely, the present invention relates to furobenzopyran derivatives of the general formula (I)

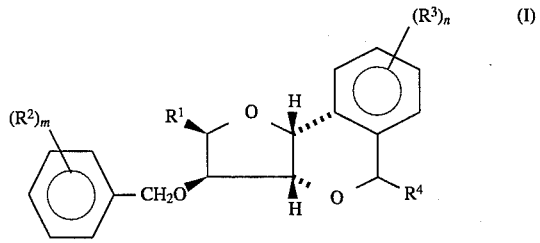

in which $R^1$ is a lower alkyl group, $R^2$ is a lower alkyl group, lower alkoxy group, halogen atom or lower alkyl group substituted by a halogen atom, $R^3$ is a lower alkyl group, lower alkoxy group, halogen atom, lower alkyl group substituted by a halogen atom, phenoxy group or benzyloxy group, $R^4$ is a hydrogen atom or lower alkyl group, m and n are any integers between 0 and 4 and each $R^2$ may be different when m is 2–4 and each $R^3$ may be different when n is 2–4, process for their preparation, herbicides which contain one or more of these compounds as an active component, and substituted tetrahydrofuran derivatives which are intermediates of compounds of the general formula (I) and have the general formula (II):

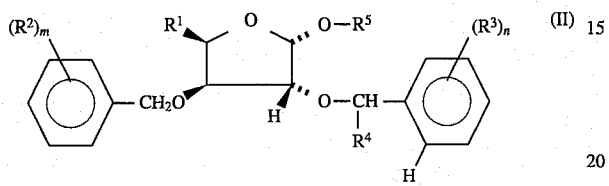

in which $R^1$, $R^2$, $R^3$, $R^4$, m and n have the above-mentioned meanings and $R^5$ is a lower alkyl group or lower acyl group.

The compounds of the general formula (I) according to the present invention are novel compounds each having a furobenzopyran ring and exhibiting high herbicidal activity and selectivity as clearly shown in the Test Examples thereinafter. If used in a rice paddy, the compounds of the present invention present sufficient selectivity to the rice plants and have a high herbicidal effect on major weeds such as *Echinochloa oryzicola, Monochoria vaginalis, Scirpus juncoides* and *Lindernia pyxidaria*. Furthermore, if used in a upland field, the compounds of the present invention present sufficient selectivity to crops such as soy beans and cotton and show high herbicidal activity on major weeds such as Echinochloa sp., *Digitaria adscendeus, Setaria viridis, Stellaria media* and *Amaranthus retroflexus*. Accordingly, the compounds of the present invention can be used for herbicides which can be effectively used in rice paddies and upland fields.

DETAILED DESCRIPTION AND THE PREFERRED EMBODIMENTS

In the compounds of the present invention, a lower alkyl group denotes an alkyl group having 1–4 carbon atoms, a lower alkoxy group denotes an alkoxy group having 1–4 carbon atoms, a lower acyl group donates an acyl group having 1–4 carbon atoms and a halogen atom denotes F, Cl, Br or I.

The compounds of the general formula (I) according to the present invention are novel compounds and are produced by an intramolecular cyclization of novel tetrahydrofuran derivatives of the general formula (II), in which the reaction takes place as follows:

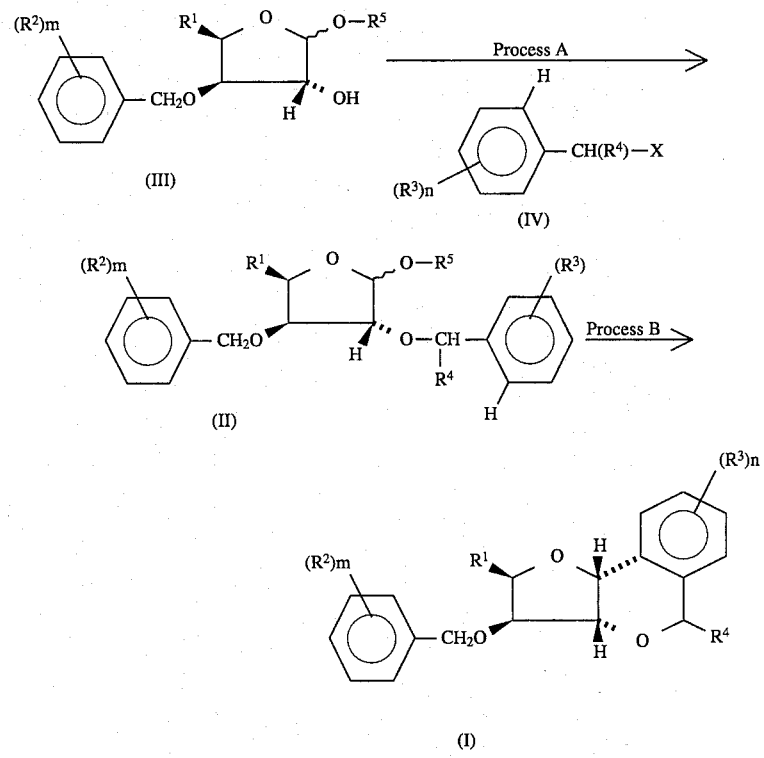

in which X represents a reactive residue such as a halogen atom and an ester residue.

The compounds of the general formula (III) are known compounds and can be easily synthesized according to the methods described in J. Org. Chem., 50, 4786 (1985) and U.S. Pat. No. 4,534,785. In general, these compounds are obtained as a mixture of alpha and beta forms; the mixture can be separated into isomers, for example by silica gel chromatography, and the isomers can be used for the subsequent reaction.

The compounds of the general formula (II) can be obtained via process A by reacting a compound of the general formula (III) (in which $R^1$, $R^2$ and m have the above-mentioned meanings and $R^5$ is a lower alkyl group or lower acyl group) with an equivalent or slightly excess amount of substituted benzyl derivative of the general formula (IV) (in which $R^3$, $R^4$ and n have the above-mentioned meanings and X is a reactive residue such as a halogen atom or an ester residue) in an inert solvent such as n-hexane, benzene, toluene, xylene, diethyl ether, dioxane, tetrahydrofuran, dimethylformamide, dimethyl sulfoxide, chlorobenzene, methylene chloride, chloroform, methyl ethyl ketone, acetone or acetonitrile, using an inorganic base such as potassium carbonate, sodium carbonate, sodium hydroxide, potassium hydroxide, sodium hydride or sodium amide. Alternatively, it is possible to carry out the reaction in a two-layer system of an organic solvent such as benzene or toluene and water in the presence of a phasetransfer catalyst such as a quaternary ammonium salt or phosphate. The reaction temperature can be between −30° C. and the boiling point of the solvent used but a temperature between room temperature and 60° C. is advantageous. After the reaction, the resultant product is treated in a conventional manner and the target compound can be purified by recrystalization or column chromatography. Further, compounds of the general formula (II), in which $R^5$ is an acyl group, can be easily synthesized from compounds of the general formula (II), in which $R^5$ is an alkyl group, by a generally known method (e.g., Chem. Ind., 27, 547, 1968).

When $R^4$ is a hydrogen atom, each compound of the general formula (II) thus obtained is a mixture of two isomers, the alpha and beta anomers, in a ratio almost the same as that of the starting material, i.e., the compounds of the general formula (III). It is possible to separate these isomers from each other by silica gel chromatography or the like and to use the resultant compounds for the subsequent reaction. When $R^4$ is a lower alkyl group, four types of diastereomers are obtained as shown in the reaction scheme below. Of these compounds, alpha and beta anomers can be separated by silica gel chromatography or the like and after the separation, the resultant compounds can be used for the subsequent reaction.

[Steric configuration of isomers of the general formula (II): when $R^4$ is a lower alkyl group]

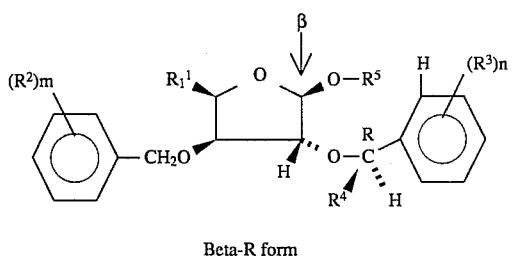

Beta-R form

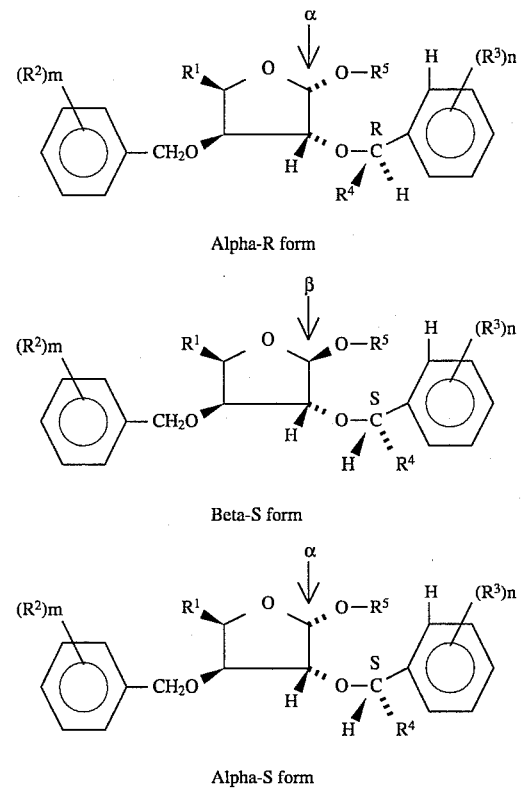

Alpha-R form

Beta-S form

Alpha-S form

The compounds of the general formula (I) according to the present invention can be obtained via process B by an intramolecular cyclization reaction of the compounds of the general formula (II) in an inert solvent such as n-hexane, nitrobenzene, chlorobenzene, methylene chloride, chloroform, carbon tetrachloride, 1,2-dichloroethane, carbon disulfide or acetonitrile in the presence of a Lewis acid such as tin tetrachloride, titanium tetrachloride, aluminum chloride, iron (III) chloride or boron trifluoride-diethyl ether complex, inorganic acid such as sulfuric acid, nitric acid, hydrochloric acid, chlorosufonic acid, phosphoric acid or organic acid such as benzenesulfonic acid or trifluoromethanesulfonic acid. The reaction temperature can be between −70° C. and the boiling point of the solvent used, but a temperature in a lower range is advantageous for the reaction and thus a preferable temperature is between −70° C. and 30° C. After the reaction, the resultant product is treated in a conventional manner and the target compound can be purified by recrystalization or column chromatography. When $R^4$ is a hydrogen atom, the compounds of the general formula (I) thus obtained are single optical isomers; when $R^4$ is an alkyl group, they are obtained as a mixture of two types of diastereomers having the following configurations:

[Steric configurations of isomers of the general formula (I) in which $R^4$ is a lower alkyl group]

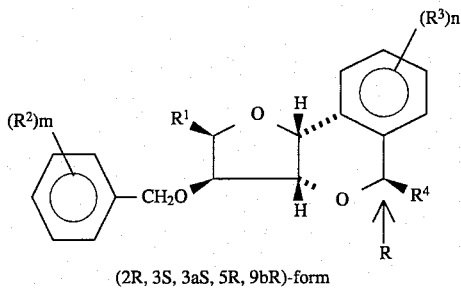

(2R, 3S, 3aS, 5R, 9bR)-form

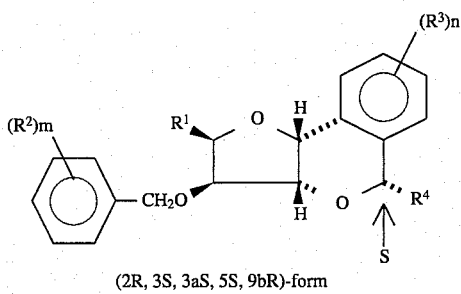

(2R, 3S, 3aS, 5S, 9bR)-form

These diastereomers can be separated by silica gel chromatography or the like. As will be shown in the Test Examples, both compounds have high herbicidal activity. Accordingly, the present invention includes also the diastereomers of the general formulae shown above.

In terms of the steric configuration of the compounds of the general formulae (I) and (II), the processes, i.e., isomer formations, when $R^4$ is a hydrogen atom and when $R^4$ is a lower alkyl group according to the present invention can be summarized as follows:

[Process when $R^4$ is a hydrogen atom]
Alpha form, beta form of the general formula (II) or the mixture thereof ↓ Step (B)

General formula (I): (2R, 3S, 3aS, 9bR)-form

[Process when $R^4$ is a lower alkyl)]
A four isomer mixture of the general formula (II):
beta-R form, beta-S form, alpha-R form and alpha-S form ↓ Step (B)

Diastereomer mixture:
(2R, 3S, 3aS, 5R, 9bR) form and (2R, 3S, 3aS, 5S, 9bR) form of the general formula (I)

Beta-R form, alpha-R form of the general formula (II) or a mixture thereof

↓ Step (B)

(2R, 3S, 3aS, 5R, 9bR)-form of the general formula (I)

Beta-S form, alpha-S form of the general formula (II) or the mixture thereof

↓ Step (B)

(2R, 3S, 3aS, 5S, 9bR)-form of the general formula (I)

When $R^4$ is a lower alkyl group, two types of diastereomers are generally obtained as described above; however, it is also possible to obtain single optical isomers using optically active compounds of the general formula (II).

Optically active compounds of the general formula (II) can be obtained, for example, by reacting optically active compounds of the general formula (IV) in step (A).

In the Examples of the present invention, when $R^4$ is a lower alkyl group, a mixture of the four isomers of compounds of the general formula (II) or the alpha or beta anomers separated from the mixture thereof are used for the reaction. The two diastereomers thus obtained are separated by silica gel chromatography (developing solvent: n-hexane/ethyl acetate); the diastereomer eluted first and the diastereomer eluted subsequently are designated as compounds of the general formula (I)-A and compounds of the general formula (I)-B, respectively. $^1$H-NMRs of the compounds of the present invention are given in Table 3. It is possible to classify the diastereomers (compounds of the general formulae (I)-A and (I)-B) based on the attributes of the protons at position 5. For example, when $R^4$ is a methyl group, protons at position 5 are observed near 4.6 ppm and 5.0 ppm for the compounds of the general formula (I)-A and the compounds of the general formula (I)-B, respectively. All the diastereomers (compounds of the general formulae (I)-A and (I)-B) have herbicidal activity as described above. A more detailed comparative test (Test Example 5) with these compounds showed that the diastereomers of compounds of the general formula (I)-A have higher herbicidal activity.

The compounds of the general formula (I) of the present invention have excellent potential as herbicides for use in rice paddies, which are sufficiently harmless to the paddy rice but exhibit a high herbicidal activity on annual weeds such as Echinochloa sp., *Cyperus difformis* L, *Monochoria vaginalis* and *Rotala indica* and perennial weeds such as *Scirpus juncoides*. Furthermore, these compounds are effective not only as herbicides in rice paddies but also as herbicides in upland fields as well as in other non-agricultural fields by soil application or by foliar application, and which present sufficient selectivity to crops such as soy beans, cotton, sugar beats, corn, sugar cane, barley, wheat, oats and rye and have a herbicidal effect on *Digitaria adscendeus, Stellaria media*, Persicaria, *Amaranthus retroflexus, Cyperus iria, Poltulaca oleracea, Senecio vulgaris, Chenopodium album, Cyperus rotundus, Calystegia japonica, Sagina japonica, Galium aparine, Alopecurusa aequalis, Poa annua, Capsella bursa pastoris, Setaria viridis*, etc.

The compounds (I) of the present invention may be applied in their pure forms onto plants to be treated; however, in general, they are mixed with inert liquids or solids and used in the forms of conventional formulations such as powders, granules, wettable powders, emulsions and flowable formulations. If necessary, auxiliary agents can be added to facilitate the formulation.

As to carriers, there is no restriction and any solid or liquid carrier which is customarily used for agricultural and horticultural formulations can be used. Examples of the solid carriers include mineral powders such as clay, talc, bentonite, calcium carbonate, diatomaceous earth and white carbon, plant powders such as soybean powder and starch, polymers such as polyvinyl alcohol and polyalkylene glycols, urea and waxes. Examples of liquid carriers include various oils, various organic solvents and water.

As to auxiliary agents, surfactants, binders, stabilizers or the like, which are customarily used in agricultural and horticultural formulations, can be used alone or in combination if appropriate. In some cases, bactericidal or fungicidal agents for industrial use can be added.

As to surfactants, non-ionic, anionic, cationic or amphoteric surfactant are conveniently used. Preferable examples are alkylphenols, higher alcohols, alkylnaphthols, higher fatty acids, fatty acid esters, polymers in which ethylene oxide and propylene oxide are polymerized with dialkylphosphoric amine or the like, alkylsulfuric ester salts (e.g., sodium lauryl sulfate), alkyl sulfonates (e.g., sodium 2-ethylhexenesufonate), and aryl sulfonates (e.g., lignin sodium sulfonate and sodium dodecylbenzene sulfonate).

The concentration of the compounds of the general formula (I) in herbicides according to the present invention varies depending on the forms of the formulations; in general, 1–20% by weight in powders, 20–60% by weight in wettable powders, 1–30% by weight in granules, 1–50% by weight in emulsions, 10–50% by weight in flowable formulations and 20–90% by weight in dry flowable formulations. The concentration of auxiliary agents is 0–80% by weight, and the concentration of carriers is calculated by subtracting the amount of active ingredients and auxiliary agents from the total, i.e., 100% by weight.

The herbicides according to the present invention are effective for any treatment methods such as a flooding soil treatment, ordinary soil treatment, mixing-phase soil treatment, and spraying of stalks and leaves. The appropriate amount for applications varies widely between 0.01 kg and 10 kg/ha of an active ingredient; a standard application preferably ranges between 0.05 and 5 kg/ha.

The herbicides according to the present invention can be used in combination with one or more other herbicides, agricultural chemicals such as insecticides and plant growth regulators, soil improvers or fertilizers and can be combined to formulate mixed formulations, thereby occasionally exerting synergistic effects. In this connection, it is particularly advantageous to use as mixtures with other herbicides.

Examples of other herbicides include phenoxyacetic acid herbicides, benzoic acid herbicides, chlorinated carboxylic acid herbicides, carbamate herbicides, urea herbicides, sulfonylurea herbicides, amide herbicides, heterocyclic herbicides (e.g., triazine herbicides and diazine herbicides), phenol herbicides, diphenyl ether herbicides, dipyridinium herbicides, dinitroaniline herbicides, organic phosphoric ester herbicides, phsphor-containing amino acid herbicides, imidazolidinone herbicides, pyridine herbicides, quinoline herbicides, sulfonamide herbicides, cyclohexanone herbicides, other organic herbicides and inorganic herbicides.

EXAMPLES

The present invention will be explained in more detail by the following Examples.

First, the process for producing the compounds of the general formula (III) is given as Reference Examples.

Reference Example 1

Preparation of methyl 5-deoxy-3-O-(2-fluorobenzyl)-5-C-methyl-D-xylofuranoside:

70.97 g of 5-deoxy-3-O-(2-fluorobenzyl)-1,2-O-isopropylidene-5-C-methyl-alpha-D-xylofuranose were dissolved in methanol (300 ml) and then 0.5 g of p-toluenesufonic acid was added therein and the mixture was refluxed for 10 hours while heating. After cooling in air, the reaction solution was neutralized with an aqueous sodium hydrogen carbonate solution and then the solvent was evaporated under reduced pressure. The resultant substance was added to water and extracted with an ether/ethyl acetate (1:1) mixed solvent. The organic phase was washed with water and then dried with anhydrous sodium sulfate. The solvent was evaporated under reduced pressure to obtain an oily product. The crude product was purified by silica gel chromatography (developing solvent: n-hexane:ethyl=3:1) and 64.21 g of the target compound were obtained as an anomeric mixture of alpha and beta forms. (Yield: 99.2%)

Reference Example 2

Preparation of methyl 5-deoxy-3-O-(2-methylbenzyl)-D-xylofuranoside:

10.68 g of 5-deoxy-3-O-(2-methylbenzyl)-1,2-O-isopropylidene-alpha-D-xylofuranose were dissolved in methanol (100 ml) and then 0.5 g of p-toluenesufonic acid was added therein and the mixture was refluxed for 10 hours while heating. After cooling in air, the reaction mixture was treated in the same manner as described in Reference Example 1 and 9.25 g of the target compound were obtained as an anomeric mixture of alpha and beta forms. (Yield: 95.6%).

Next, the preparation of compounds of the general formula (II) and of the general formula (I) of the present invention will be described as Examples.

Example 1

Preparation of (2R,3S,3aS,9bR)-2-ethyl-3-(2-fluorobenzyloxy)- 3,3a,5,9b-tetrahydro-2H-furo[3,2-c][2]benzopyran (compound No. 1 of the general formula (I)):
1) Preparation of methyl 2-O-benzyl-5-deoxy-3-O-(2-fluorobenzyl)-5C-methyl-D-xylofuranoside (compounds Nos. 1, 2 and 3 of the general formula (II)):

25.0 g of methyl 5-deoxy-3-O-(2-fluorobenzyl)-5-C-methyl-D-xylofuranoside obtained in Reference Example 1 were dissolved in 200 ml of tetrahydrofuran and 4.44 g of oil sodium hydride (containing 40% liquid paraffin) were gradually added while stirring. After adding 1.0 g of tetrabutylammonium iodide and 18.98 g of benzylbromide, the resulting mixture was stirred at room temperature for 4 hours. The solvent was evaporated under reduced pressure and the crude product thus obtained was added to water and extracted with ether. The organic phase was thoroughly washed and then dried with anhydrous sodium sulfate. The solvent was evaporated under reduced pressure to obtain an oily product. The crude product was purified by silica gel chromatography (developing solvent: n-hexane:ethyl acetate=10:1) and 30.4 g of the target compound were obtained as an anomeric mixture of alpha and beta forms. (Yield: 91.2%).

The anomeric mixture of alpha and beta forms thus obtained was further purified by silica gel chromatography (developing solvent: n-hexane:ethyl acetate=15:1) and separated into alpha form and beta form fractions.
2) Preparation of (2R,3S,3aS,9bR)-2-ethyl-3-(2-fluorobenzyloxy)- 3,3a,5,9b-tetrahydro-2H-furo[3,2-c][2]benzopyran:

3.04 g of methyl 2-O-benzyl-5-deoxy-3-O-(2-fluorobenzyl)-5-C-methyl-D-xylouranoside obtained in 1) (a mixture of alpha and beta forms) were dissolved in 20 ml of dichloromethane and 3.59 g of boron trifluoride-diethyl ether complex were added under cooling with ice. The resulting mixture was stirred at room temperature for 2 hours and then poured into a saturated aqueous sodium hydrogen carbonate solution with ice. The organic phase was thoroughly washed with water and then dried with anhydrous sodium sulfate. The solvent was evaporated under reduced pressure to obtain an oily product. The crude product was purified by silica gel chromatography (developing solvent: n-hexane:ethyl acetate=5:1) and 2.39 g of the target compound were obtained. (Yield: 86.4%).

Example 2

Preparation of (2R,3S,3aS,9bR)-2-ethyl-3-(2-fluorobenzyloxy)- 3,3a,5,9b-tetrahydro-2H-furo[3,2-c][2]benzopyran (compound No. 1 of the general formula (I)):
1) Preparation of 1-O-acetyl-2-O-benzyl-5-deoxy-3-O-(2 -fluorobenzyl)-5-C-methyl-D-xylofuranoside (compound No. 26 of the general formula (II)):

4.00 g of methyl 2-O-benzyl-5-deoxy-3-O-(2-fluorobenzyl)-5-C-methyl-D-xylofuranoside obtained in Example 1-1) were dissolved in 15 ml of acetic acid and 3.5 ml of acetic anhydride and 0.75 ml of conc. sulfuric acid was added under cooling with ice. After stirring at room temperature for 12 hours, the mixture was poured into ice water and extracted with chloroform. The organic phase was washed with water, a saturated aqueous sodium hydrogen carbonate solution and saturated salt water and then dried with anhydrous sodium sulfate. The solvent was evaporated under reduced pressure to obtain an oily product. The crude product was purified by silica gel chromatography (developing solvent: n-hexane:ethyl acetate=3:1) and 3.43 g of the target compound were obtained as an anomeric mixture of alpha and beta forms. (Yield: 79.6%).

2) Preparation of (2R,3S,3aS,9bR)-2-ethyl-3-(2-fluorobenzyloxy)-3,3a,5,9b-tetrahydro-2H-furo[3,2-c][2]benzopyran 1.94 g of 1-O-acetyl-2-O-benzyl-5-deoxy-3-O-(2 -fluorobenzyl)-5-C-methyl-D-xylofuranoside obtained in 1) were dissolved in 20 ml of dichloromethane and 2.13 g of boron trifluoride-diethyl ether complex were added under cooling with ice. The resulting mixture was stirred at room temperature for 2 hours and then poured into a saturated aqueous sodium hydrogen carbonate solution with ice. The organic phase was thoroughly washed with water and then dried with anhydrous sodium sulfate. The solvent was evaporated under reduced pressure to obtain an oily product. The crude product was purified by silica gel chromatography (developing solvent: n-hexane:ethyl acetate=5:1) and 1.51 g of the target compound were obtained. (Yield: 92.3%).

Example 3

Preparation of (2R,3S,3aS,9bR)-2-ethyl-3-(2-fluorobenzyloxy)- 6-methyl-3,3a,5,9b-tetrahydro-2H-furo[3,2-c][2]benzopyran (compound No. 2 of the general formula (I)):
1) Preparation of methyl 5-deoxy-3-O-(2-fluorobenzyl)-5 -C-methyl-2-O-(2-methylbenzyl)-D-xylofuranoside (compound No. 4 of the general formula (II):

2.5 g of methyl 5-deoxy-3-O-(2-fluorobenzyl)-5 -C-methyl-D-xylofuranoside obtained in Reference Example 1 were dissolved in 15 ml of dimethylformamide and 0.44 g of sodium hydroxide was added while stirring. 1.95 g of 2-methylbenzyl bromide was added therein and then the resulting mixture was stirred at room temperature for 5 hours. A crude product obtained in the same manner as described in Example 1-1) was purified by silica gel chromatography (developing solvent: n-hexane:ethyl acetate= 10:1) and 3.22 g of the target compound were obtained as an anomeric mixture of alpha and beta forms. (Yield: 93.0%).

2) Preparation of (2R,3S,3aS,9bR)-2-ethyl-3-(2-fluorobenzyloxy)-6-methyl-3,3a,5,9b-tetrahydro-2H-furo[3,2-c][2] benzopyran:

1.02 g of methyl 5-deoxy-3-O-(2-fluorobenzyl)-5 -C-methyl-2-O-(2-methylbenzyl)-D-xylofuranoside obtained in 1) were dissolved in 12 ml of chloroform and 8.17 ml of titanium tetrachloride (a 1.0M dichloromethane solution) were added under cooling with ice. The resulting mixture was stirred at room temperature for 2 hours and then poured into a saturated aqueous sodium hydrogen carbonate solution with ice. The organic phase was thoroughly washed with water and then dried with anhydrous sodium sulfate. The solvent was evaporated under reduced pressure to obtain an oily product. The crude product was purified by silica gel chromatography (developing solvent: n-hexane:ethyl acetate=5:1) and 0.66 g of the target compound was obtained. (Yield: 71.0%)

Example 4

Preparation of (2R,3S,3aS,9bR)-2-ethyl-3-(2-fluorobenzyloxy)- 7-methyl-3,3a,5,9b-tetrahydro-2H-furo[3,2-c][2]benzopyran (compound No. 3 of the general formula (I)):
1) Preparation of methyl 5-deoxy-3-O-(2-fluorobenzyl)-5 -C-methyl-2-O-(3-methylbenzyl)-D-xylofuranoside (compound Nos. 5, 6 and 7 of the general formula (II)):

2.5 g of methyl 5-deoxy-3-O-(2-fluorobenzyl)-5 -C-methyl-D-xylofuranoside obtained in Reference Example 1 were dissolved in 20 ml of tetrahydrofuran and 0.44 g of oil sodium hydride (containing 40% liquid paraffin) was gradually added while stirring. 0.1 g of tetrabutylammonium iodide and 1.95 g of 3-methylbenzyl bromide were added therein and then the resulting mixture was stirred at room temperature for 3 hours. A crude product obtained in the same manner as described in Example 1-1) was purified by silica gel chromatography (developing solvent: n-hexane:ethyl acetate=10:1) and 3.13 g of the target compound were obtained as an anomeric mixture of alpha and beta forms. (Yield: 90.5%).

The anomeric mixture of alpha and beta forms was further purified by silica gel chromatography (developing solvent: n-hexane:ethyl acetate=15:1) and separated into the alpha and beta forms.

2) Preparation of (2R,3S,3aS,9bR)-2-ethyl-3-(2-fluorobenzyloxy)-7-methyl-3,3a,5,9b-tetrahydro-2H-furo[3,2-c][2] benzopyran:

0.62 g of methyl 5-deoxy-3-O-(2-fluorobenzyl)-5 -C-methyl-2-O-(3-methylbenzyl)-D-xylofuranoside (a mixture of alpha and beta forms) obtained in 1) was dissolved in 10 ml of acetonitrile and 4.97 ml of tin tetrachloride (a 1.0M dichloromethane solution) were added under cooling with ice. The resulting mixture was stirred at room temperature for 3 hours and then poured into a saturated aqueous sodium hydrogen carbonate solution with ice. The organic phase was thoroughly washed with water and then dried with anhydrous sodium sulfate. The solvent was evaporated under reduced pressure to obtain an oily product. The crude product was purified by silica gel chromatography (developing solvent: n-hexane:ethyl acetate=5:1) and 0.39 g of the target compound was obtained. (Yield: 68.4%)

Example 5

Preparation of (2R,3S,3aS,9bR)-2-ethyl-3-(2-fluorobenzyloxy)- 8-methyl-3,3a,5,9b-tetrahydro-2H-furo[3,2-c][2]benzopyran (compound No. 4 of the general formula (I)):
1) Preparation of methyl 5-deoxy-3-O-(2-fluorobenzyl)-5 -C-methyl-2-O-(4-methylbenzyl)-D-xylofuranoside (compounds No. 8, 9 and 10 of the general formula (II)):

2.5 g of methyl 5-deoxy-3-O-(2-fluorobenzyl)-5 -C-methyl-D-xylofuranoside obtained in Reference Example 1 were dissolved in 20 ml of tetrahydrofuran and 0.44 g of oil sodium hydride (containing 40% liquid paraffin) was gradually added while stirring. 0.1 g of tetrabutylammonium iodide and 1.95 g of 4-methylbenzyl bromide were added therein and then the resulting mixture was stirred at room temperature for 3 hours. A crude product obtained in the same manner as described in Example 1-1) was purified by silica gel chromatography (developing solvent: n-hexane:ethyl acetate=10:1) and 3.19 g of the target compound were obtained as an anomeric mixture of alpha and beta forms. (Yield: 92.0%).

The anomeric mixture of alpha and beta forms was further purified by silica gel chromatography (developing solvent: n-hexane:ethyl acetate=15:1) and separated into the alpha and beta forms.

2) Preparation of (2R,3S,3aS,9bR)-2-ethyl-3-(2-fluorobenzyloxy)-8-methyl-3,3a,5,9b-tetrahydro-2H-furo[3,2-c][2]benzopyran:

0.51 g of methyl 5-deoxy-3-O-(2-fluorobenzyl)-5 -C-methyl-2-O-(4-methylbenzyl)-D-xylofuranoside obtained in 1) was dissolved in 10 ml of 1,2-dichloroethane and 0.55 g of aluminum chloride was added under cooling with ice. The resulting mixture was stirred at room temperature for 3 hours and then poured into a saturated aqueous sodium hydrogen carbonate solution with ice. The organic phase was thoroughly washed with water and then dried with anhydrous sodium sulfate. The solvent was evaporated under reduced pressure and an oily crude product was obtained. The crude product was purified by silica gel chromatography (developing solvent: n-hexane:ethyl acetate=5:1) and 0.40 g of the target compound was obtained. (Yield: 85.1%)

Example 6

Preparation of (2R,3S,3aS,9bR)-2-ethyl-3-(2-fluorobenzyloxy)-5-methyl-3,3a,5,9b-tetrahydro-2H-furo[3,2-c][2]benzopyran (compound Nos. 8-A and 8-B of the general formula (I)):

1) Preparation of methyl 5-deoxy-3-O-(2-fluorobenzyl)-5 -C-methyl-2-O-(1-phenylethyl)-D-xylofuranoside (compound No. 20 of the general formula (II)):

3.00 g of methyl 5-deoxy-3-O-(2-fluorobenzyl)-5 -C-methyl-D-xylofuranoside obtained in Reference Example 1 and 4.52 g of alpha-phenylethyl bromide were dissolved in 40 ml of N,N-dimethylformamide and 1.11 g of oil sodium hydride (containing 40% liquid paraffin) was gradually added while stirring under nitrogen flow, after which the mixture was stirred at 60° C. for 2 hours. The reaction mixture was poured into ice water, neutralized with dilute hydrochloric acid, and then extracted with a mixed solvent, n-hexane:ethyl acetate=9:1 (v/v). The organic phase was thoroughly washed with water and a saturated aqueous sodium hydrogen carbonate solution and then dried with anhydrous sodium sulfate. The solvent was evaporated under reduced pressure and the resultant crude product was purified by silica gel chromatography (developing solvent: n-hexane:ethyl acetate=9:1) and 3.55 g of the target compound were obtained as a mixture of four kinds of diastereomers. (Yield: 85.3%).

2) Preparation of (2R,3S,3aS,9bR)-2-ethyl-3-(2-fluorobenzyloxy)-5-methyl-3,3a,5,9b-tetrahydro-2H-furo[3,2-c][2]benzopyran:

2.60 g of methyl 5-deoxy-3-O-(2-fluorobenzyl)-5 -C-methyl-2-O-(1-phenylethyl)-D-xylofuranoside obtained in 1) were dissolved in 30 ml of dichloromethane and 2.95 g of boron trifluoride-diethyl ether complex were gradually added at −50° C. while stirring. The resulting mixture was warmed up to room temperature, stirred for 2 hours and then poured into a saturated aqueous sodium hydrogen carbonate solution with ice. The organic phase was thoroughly washed with water and then dried with anhydrous sodium sulfate. The solvent was evaporated under reduced pressure to obtain an oily product. The crude product was purified by silica gel chromatography (developing solvent: n-hexane:ethyl acetate=20:1) and the target compounds, 1.08 g of 8-A (yield: 45.5%) and 0.98 g of 8-B (yield: 41.2%), were obtained.

Example 7

Preparation of (2R,3S,3aS,9bR)-2-methyl-3-(2-methylbenzyloxy)-7-methoxy-3,3a,5,9b-tetrahydro-2H-furo[3,2-c][2]benzopyran (compound No. 20 of the general formula (I)) and (2R,3S,3aS,9bR)-2-methyl-3-(2-methylbenzyloxy)-9-methoxy- 3,3a,5,9b-tetrahydro-2H-furo[3,2-c][2]benzopyran (compound No. 21 of the general formula (I)):

1) Preparation of methyl 5-deoxy-2-O-(3-methoxybenzyl)-3-O-( 2-methylbenzyl)-alpha-D-xylofuranoside (compound No. 27 of the general formula (II)):

1.0 g of methyl 5-deoxy-3-O-(2-methylbenzyl)-alpha-D-xylofuranoside obtained in Reference Example 2 was dissolved in 20 ml of tetrahydrofuran and 0.17 g of oil sodium hydride (containing 40% liquid paraffin) was gradually added while stirring. 0.1 g of tetrabutylammonium iodide and 0.68 g of m-methoxybenzyl chloride were added therein and the mixture was stirred at room temperature for 4 hours. The solvent was evaporated under reduced pressure and a crude product thus obtained was added to water and extracted with ether. The organic phase was thoroughly washed with water and then dried with anhydrous sodium sulfate. The solvent was evaporated under reduced pressure and then an oily crude product was obtained. This crude product was purified by silica gel chromatography (developing solvent: n-hexane:ethyl acetate=10:1) and 1.2 g of the target compound were obtained. (Yield: 81.3%).

2) Preparation of (2R,3S,3aS,9bR)-2-methyl-3-(2-methylbenzyloxy)-7-methoxy-3,3a,5,9b-tetrahydro-2H-furo[3,2-c][2]benzopyran and (2R,3S,3aS,9bR)-2-methyl-3-(2-methylbenzyloxy)-9 -methoxy-3,3a,5,9b-tetrahydro-2H-furo[3,2-c][2]benzopyran:

0.85 g of methyl 2-O-(3-methoxybenzyl)-5-deoxy-3-O-( 2-methylbenzyl)-alpha-D-xylofuranoside obtained in 1) was dissolved in 50 ml of dichloromethane and 0.70 g of boron trifluoride-diethyl ether complex was added under cooling with ice. The resulting mixture was stirred at room temperature for 2 hours and then poured into a saturated aqueous sodium hydrogen carbonate solution with ice. The organic phase was thoroughly washed with water and then dried with anhydrous sodium sulfate. The solvent was evaporated under reduced pressure to obtain an oily product. This crude product was purified by silica gel chromatography (developing solvent: n-hexane:ethyl acetate=5:1) and the target compounds, 0.42 g of compound No. 20 (yield: 52.5%) and 0.13 g of compound No. 21 (yield: 16.3%) were obtained.

Example 8

Preparation of (2R,3S,3aS,9bR)-2-ethyl-3-(2-methylbenzyloxy)- 5-methyl-7-methoxy-3,3a,5,9b-tetrahydro-2H-furo[3,2-c][2]benzopyran (compound Nos. 49-A and 49-B of the general formula (I)) and (2R,3S,3aS,9bR)-2-ethyl-3-(2 -methylbenzyloxy)-5-methyl-9-methoxy-3,3a,5,9b-tetrahydro-2H-furo[3,2-c][2]benzopyran (compound Nos. 50-A and 50-B of the general formula (I)):

1) Preparation of methyl 5-deoxy-3-O-(2-methylbenzyl)-5 -C-methyl-2-O-{1-(3-methoxyphenyl)ethyl}-beta-D-xylofuranoside (compound No. 36 of the general formula (II)):

7.96 g of methyl 5-deoxy-3-O-(2-methylbenzyl)-5 -C-methyl-beta-D-xylofuranoside obtained in the same manner as described in Reference Example 1 and 16.0 g of alpha- (3-methoxyphenyl)ethyl bromide were dissolved in 100 ml of N,N-dimethylformamide and 3.60 g of oil sodium hydride (containing 40% liquid paraffin) were added while stirring under nitrogen flow. After the addition was completed, the mixture was stirred at 50° C. for 2 hours. The reaction mixture was poured into ice water, neutralized with dilute hydrochloric acid, and then extracted with a mixed solvent, n-hexane:ethyl acetate=9:1(v/v). The organic phase was thoroughly washed with water and a saturated aqueous sodium hydrogen carbonate solution and then dried with anhydrous sodium sulfate. The solvent was evaporated under reduced pressure and the resultant crude product was purified by silica gel chromatography (developing solvent: n-hexane:ethyl acetate=8:1) and 5.50 g of the target compound were obtained as a mixture of two kinds of diastereomers. (Yield: 45.8%).

2) Preparation of (2R,3S,3aS,9bR)-2-ethyl-3-(2-methylbenzyloxy)- 5-methyl-7-methoxy-3,3a,5,9b-tetrahydro-2H-furo[3,2 -c][2]benzopyran and (2R,3S,3aS,9bR)-2-ethyl-3-(2-methylbenzyloxy)-5-methyl-9-methoxy-3,3a,5,9b-tetrahydro-2H-furo[3,2 -c][2]benzopyran:

5.30 g of methyl 5-deoxy-3-O-(2-methylbenzyl)-5-C-methyl-2-O-{1-(3-methoxyphenyl)ethyl}-beta-D-xylofuranoside obtained in 1) were dissolved in 100 ml of dichloromethane and a dicholomethane solution (20 ml) of 4.70 g of boron trifluoride-diethyl ether complex were gradually added at −60° C. while stirring. The resulting mixture was warmed up to room temperature for 2 hours and then poured into a saturated aqueous sodium hydrogen carbonate solution with ice. The organic phase was thoroughly washed with water and then dried with anhydrous sodium sulfate. The solvent was evaporated under reduced pressure to obtain an oily product. This crude product was purified by flash chromatography (FC-40, developing solvent n-hexane:ethyl acetate=6:1) and the target compounds, 1.65 g of 49-A (yield: 33.8%), 0.98 g of 49-B (yield: 20.1%), 0.42 g of 50-A (yield: 8.6%) and 0.5 g of 50-B (yield: 10.2%), were obtained.

Examples 9–63

In Examples 9–63, compound Nos. 5–7, 9–19, 22-A–48-A and 51–68B of the general formula (I) were prepared in the same manner as described in Examples 1–8. Structures of the compounds of the general formula (II) prepared in these Examples are given in Table 1, their physical properties are shown in Table 2 and the physical properties of the compounds of the general formula (I) of the present invention are shown in Table 3.

TABLE 1

Compounds in general formula (II)

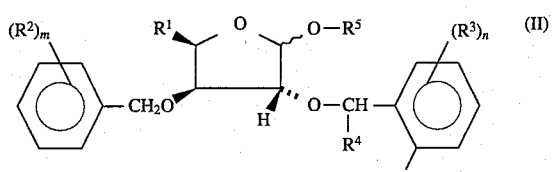

| Compound No. | $R^1$ | $(R^2)_m$ | $(R^3)_n$ | $R^4$ | $R^5$ | Remarks |
|---|---|---|---|---|---|---|
| 1 | $C_2H_5$ | o-F | H | H | $CH_3$ | αβ mixture |

TABLE 1-continued

Compounds in general formula (II)

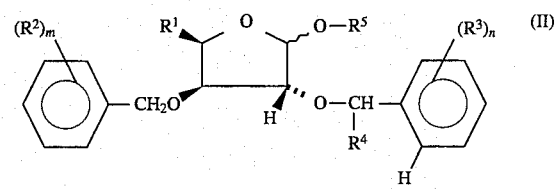

| Compound No. | $R^1$ | $(R^2)_m$ | $(R^3)_n$ | $R^4$ | $R^5$ | Remarks |
|---|---|---|---|---|---|---|
| 2 | $C_2H_5$ | o-F | H | H | $CH_3$ | α |
| 3 | $C_2H_5$ | o-F | H | H | $CH_3$ | β |
| 4 | $C_2H_5$ | o-F | o-$CH_3$ | H | $CH_3$ | αβ mixture |
| 5 | $C_2H_5$ | o-F | m-$CH_3$ | H | $CH_3$ | αβ mixture |
| 6 | $C_2H_5$ | o-F | m-$CH_3$ | H | $CH_3$ | α |
| 7 | $C_2H_5$ | o-F | m-$CH_3$ | H | $CH_3$ | β |
| 8 | $C_2H_5$ | o-F | p-$CH_3$ | H | $CH_3$ | αβ mixture |
| 9 | $C_2H_5$ | o-F | p-$CH_3$ | H | $CH_3$ | α |
| 10 | $C_2H_5$ | o-F | p-$CH_3$ | H | $CH_3$ | β |
| 11 | $C_2H_5$ | o-F | m-$OCH_3$ | H | $CH_3$ | αβ mixture |
| 12 | $C_2H_5$ | o-F | o-F | H | $CH_3$ | α |
| 13 | $C_2H_5$ | o-F | m-F | H | $CH_3$ | α |
| 14 | $C_2H_5$ | o-F | m-F | H | $CH_3$ | β |
| 15 | $C_2H_5$ | o-F | m-Cl | H | $CH_3$ | αβ mixture |
| 16 | $C_2H_5$ | o-F | o-$CH_2Br$ | H | $CH_3$ | αβ mixture |
| 17 | $C_2H_5$ | o-F | m-OPh | H | $CH_3$ | αβ mixture |
| 18 | $C_2H_5$ | o-F | 2-$CH_3$ 4-$CH_3$ | H | $CH_3$ | αβ mixture |
| 19 | $C_2H_5$ | o-F | 3-$CH_3$ 4-$CH_3$ | H | $CH_3$ | αβ mixture |
| 20 | $C_2H_5$ | o-F | H | $CH_3$ | $CH_3$ | αβ mixture |
| 21 | $C_2H_5$ | o-Cl | m-$CH_3$ | H | $CH_3$ | αβ mixture |
| 22 | $C_2H_5$ | o-Cl | m-$OCH_3$ | H | $CH_3$ | αβ mixture |
| 23 | $C_2H_5$ | o-Cl | p-$CH_2CH_3$ | H | $CH_3$ | αβ mixture |
| 24 | $CH_3$ | o-F | H | H | $CH_3$ | α |
| 25 | $CH_3$ | o-F | H | $CH_3$ | $CH_3$ | αβ mixture |
| 26 | $C_2H_5$ | o-F | H | H | $COCH_3$ | αβ mixture |
| 27 | $CH_3$ | o-$CH_3$ | m-$OCH_3$ | H | $CH_3$ | α |
| 28 | $C_2H_5$ | o-F | m-Br | H | $CH_3$ | αβ mixture |
| 29 | $C_2H_5$ | o-Cl | H | $C_2H_5$ | $CH_3$ | β |
| 30 | $C_2H_5$ | o-F | o-$CH_3$ | $CH_3$ | $CH_3$ | β |
| 31 | $C_2H_5$ | o-F | m-$OCH_3$ | $CH_3$ | $CH_3$ | β |
| 32 | $C_2H_5$ | o-F | m-Cl | $CH_3$ | $CH_3$ | β |
| 33 | $C_2H_5$ | o-Cl | H | $CH_3$ | $CH_3$ | α |
| 34 | $C_2H_5$ | o-Cl | H | $CH_3$ | $CH_3$ | β |
| 35 | $C_2H_5$ | o-Cl | m-$OCH_3$ | $CH_3$ | $CH_3$ | α |
| 36 | $C_2H_5$ | o-$CH_3$ | m-$OCH_3$ | $CH_3$ | $CH_3$ | β |

TABLE 2

Physical properties of the compound in general formula (II)

| Compound No. | Physical properties [NMR(400MHz, $CDCl_3$); δ ppm] |
|---|---|
| 1 | 0.95(3H, t, J=7.3Hz), 1.57–1.73(2H, m), 3.41(3H, s), 3.95–4.16(3H, m), 4.54–4.71(4H, m), 4.82(1/2H, d, J=4.4Hz), 4.88(1/2H, d, J=2.2Hz), 7.00–7.43(9H, m) |
| 2 | 0.95(3H, t, J=7.3Hz), 1.57–1.71(2H, m), 3.41(3H, s), 3.97–4.16(H, m), 4.54–4.71(4H, m), 4.82(1H, d, J= 4.4Hz), 7.00–7.40(9H, m) |
| 3 | 0.95(3H, t, J=7.3Hz), 1.63–1.75(2H, m).3.41(3H, s), 3.95–3.97(1H, m), 4.00(1H, d, J=2.2Hz), 4.02–4.10 (1H, m), 4.55–4.67(4H, m), 4.88(1H, d, J=2.2Hz), 7.01–7.43(9H, m) |
| 4 | 0.95(3H, t, J=7.3Hz), 1.57–1.71(2H, m), 2.33(3/2H, s), 2.38(3/2H, s), 3.41(3/2H, s), 3.42(3/2H, s), 3.94– 4.15(3H, m), 4.51–4.70(4H, m), 4.85(1/2H, d, J= 4.4Hz), 4.88(1/2H, d, J=2.2Hz), 6.99–7.43(8H, m) |
| 5 | 0.95(3H, t, J=7.3Hz), 1.57–1.73(2H, m), 2.34(3/2H, |

TABLE 2-continued

Physical properties of the compound in general formula (II)

| Compound No. | Physical properties [NMR(400MHz, CDCl₃); δ ppm] |
|---|---|
|  | s), 2.35(3/2H, s), 3.40(3/2H, s), 3.41(3/2H, s), 3.95–4.16(3H, m), 4.51–4.71(4H, m), 4.81(1/2H, d, J=4.4Hz), 4.88(1/2H, d, J=2.2Hz), 7.00–7.44(8H, m) |
| 6 | 0.95(3H, t, J=7.3Hz), 1.57–1.69(2H, m), 2.34(3H, s), 3.40(3H, s), 3.96–.4.16(3H, m), 4.53–4.71(4H, m), 4.81 (1H, d, J=4.4Hz), 7.00–7.41(8H, m) |
| 7 | 0.95(3H, t, J=7.3Hz), 1.59–1.74(2H, m), 2.35(3H, s), 3.41(3H, s), 3.95–4.10(3H, m), 4.51–4.68(4H, m), 4.88 (1H, d, J=2.2Hz), 7.01–7.44(8H, m) |
| 8 | 0.95(3H, t, J=7.3Hz), 1.54–1.72(2H.m), 2.34(3H, s), 3.40(3/2H, s), 3.41(3/2H, s), 3.93–4.15(3H, m), 4.50–4.69(4H, m), 4.80(1/2H, d, J=4.4Hz), 4.87(1/2H, d, J=2.2Hz), 7.00–7.43(8H, m) |
| 9 | 0.94(3H, t, J=7.3Hz), 1.54–1.70(2H, m), 2.34(3H, s), 3.40(3H, s), 3.95–4.15(3H, m), 4.53–4.69(4H, m), 4.80 (1H, d, J=4.4Hz), 7.00–7.40(8H, m) |
| 10 | 0.95(3H, t, J=7.3Hz), 1.59–1.73(2H, m), 2.34(3H, s), 3.41(3H, s), 3.93–4.13(3H, m), 4.50–4.66(4H, m), 4.87 (1H, d, J=2.2Hz), 7.01–7.43(8H, m) |
| 11 | 0.95(3H, t, J=7.3Hz), 1.66–1.71(2H, m), 3.41(3H, s), 3.79(3/2H, s), 3.80(3/2H, s), 3.95–4.17(3H, m), 4.56–4.72(4H, m), 4.81–4.88(1H, m), 6.82–7.41(8H, m) |
| 12 | 0.95(3H, t, J=7.3Hz), 1.56–1.72(2H, m), 3.41(3H, s), 3.97–4.04(1H, m), 4.08–4.16(2H, m), 4.54–4.74(4H, m), 4.89(1H, d, J=4.4Hz), 7.00–7.49(8H, m) |
| 13 | 0.96(3H, t, J=7.3Hz), 1.59–1.69(2H, m), 3.42(3H, s), 3.96–4.02(1H, m), 4.10–4.17(2H, m), 4.55–4.71(4H, m), 4.85(1H, d, J=4.4Hz), 6.98–7.42(8H, m) |
| 14 | 0.96(3H, t, J=7.3Hz), 1.58–1.73(2H, m), 3.42(3H, s), 3.96–4.00(2H, m), 4.08(1H, dd, J=7.3, 12.5Hz), 4.57–4.68(4H, m), 4.87(1H, d, J=2.2Hz), 6.96–7.44(8H, m) |
| 15 | 0.99(3H, t, J=7.3Hz), 1.61–1.77(2H, m), 3.42(3H, s), 3.98–4.21(3H, m), 4.53–4.87(5H, m), 7.20–7.49(8H, m) |
| 16 | 0.96(3H, t, J=7.3Hz).1.55–1.73(2H, m), 3.42(3/2H, s), 3.43(3/2H, s), 3.98–4.16(3H, m), 4.54–4.91(7H, m), 7.00–7.44(8H, m) |
| 17 | 0.95(3H, t, J=7.3Hz), 1.50–1.71(2H, m), 3.39(3/2H, s), 3.40 (3/2H, s), 3.92–4.15(3H, m), 4.52–4.68(4H, m), 4.81–4.87(1H, m), 6.93–7.42(13H, m) |
| 18 | 0.86–0.99(3H, m), 1.50–1.75(2H, m), 2.30–2.42(6H, m), 3.41 (3/2H, s), 3.42(3/2H, s), 3.92–4.13(3H, m), 4.50–4.89(5H, m), 6.94–7.42(7H, m) |
| 19 | 0.86–0.97(3H, m), 1.50–1.74(2H, m), 2.20–2.30(6H, m), 3.35–3.44(3H, m), 3.95–4.15 (3H, m), 4.49–4.89(5H, m), 7.00–7.43 (7H, m) |
| 20 | 0.89–1.03(3H, m), 1.23–1.75(5H, m), 3.21–3.56(3H, m), 3.79–5.08(7H, m), 6.97–7.47(9H, m) |
| 21 | 0.95–1.01(3H, m), 1.58–1.78(2H, m), 2.33(3/2H, s), 2.34(3/2H, s), 3.41(3/2H, s), 3.42(3/2H, s), 3.98–4.19 (3H, m), 4.53–4.75(4H, m), 4.83(1/2H, d, J=4.4Hz), 4.89(1/2H, d.J=1.5Hz), 7.09–7.50(8H, m) |
| 22 | 0.98(3H, t, J=7.3Hz), 1.60–1.77(2H.m), 3.41(3H, s), 3.77(3/2H, s), 3.78(3/2H, s), 3.99–4.20(3H, m), 4.53–4.90(5H, m), 6.81–6.96(3H, m), 7.18–7.49(5H, m) |
| 23 | 0.97(3H, t, J=7.3Hz), 1.21(3H, t, J=7.3Hz), 1.60–1.78(2H, m), 2.60–2.77(2H, m), 3.42(3H, s), 3.97–4.18 (3H, m), 4.53–4.90(5H, m), 7.15–7.50(8H, m) |
| 24 | 1.23(3H, d, J=6.6Hz), 3.39(3H, s), 3.96–4.40(3H, m), 4.58–4.69(4H, m), 4.77(1H, d, J=4.4Hz), 7.01–7.43 (9H, m) |
| 25 | 1.18–1.51(6H, m), 3.20–5.05(1OH, m), 6.80–7.50(9H, m) |
| 26 | 0.96(3H, t, J=7.4Hz), 1.54–1.73(2H, m), 2.10(3/2H, s), 2.12(3/2H, s), 3.95–4.18(3H, m), 4.51–4.71(4H, m), 6.25(1/2H, d, J=2.2Hz), 6.37(1/2H, d, J=4.6Hz), 7.00–7.44(9H, m) |
| 27 | 1.23(3H, d, J=6.6Hz), 2.30(3H, s), 3.40(3H, s), 3.78 (3H, s), 3.97–3.99(1H, m), 4.14–4.17(1H, m), 4.34–4.41(1H, m), 4.48–4.65(4H, m), 4.78(1H, d, J=4.6Hz), 6.82–7.34(8H, m) |
| 28 | 0.95(3H, t, J=7.7Hz), 1.65–1.72(2H, m), 3.41(3H, s), 3.95–3.99(1H, m), 4.04–4.15(2H, m), 4.52–4.68(4H, m), 4.83–4.86(1H, m), 7.01–7.53(8H, m) |
| 29 | 0.86–0.99(6H, m), 1.63–1.85(4H, m), 3.18(3/2H, s), 3.42(3/2H, s), 3.84–3.96(2H, m), 4.07–4.13(1H, m), 4.24–4.40(2H, m), 4.59–4.69(3/2H, m), 4.91(1/2H, d, J=1.5Hz), 7.17–7.51(9H, m) |
| 30 | 0.89–0.95(3H, m), 1.40–1.43(3H, m), 1.61–1.69(2H, m), 2.31(3H, s), 3.23(3/2H, s), 3.42(3/2H, s), 3.80–3.95 (2H, m), 4.04–4.13(1H, m), 4.34–4.45(1H, m), 4.55–4.65(1H, m), 4.70–4.91(2H, m), 6.98–7.48(8H, m) |
| 31 | 0.89–0.95(3H, m), 1.42–1.46(3H, m), 1.60–1.70(2H, m), 3.25(3/2H, s), 3.42(3/2H, s), 3.78(3/2H, m), 3.81 (3/2H, m), 3.83–3.91(2H, m), 4.03–4.08(1H, m), 4.31–4.44(1H, m), 4.50–4.66(2H, m), 4.71(1/2H, s), 4.89 (1/2H, d, J=1.5Hz), 6.30–7.45(8H, m) |
| 32 | 0.90–1.03(3H, m), 1.40–1.44(3H, m), 1.61–1.70(2H, m), 3.26(3/2H, s), 3.42(3/2H, s), 3.85–4.19(3H, m), 4.36–5.08(4H, m), 6.98–7.45(8H, m) |
| 33 | 0.92–0.97(3H, m), 1.50–1.61(5H, m), 3.21(3/2H, s), 3.48(3/2H, s), 3.82–4.25(3H, m), 4.44–4.93(4H, m), 7.18–7.53(9H, m) |
| 34 | 0.93–1.00(3H, m), 1.45–1.76(5H, m).3.21(3/2H, s), 3.42 (3/2H, s), 3.86–4.14(3H, m), 4.33–4.92(4H, m), 7.17–7.51(9H, m) |
| 35 | 0.91–0.97(3H, m), 1.49–1.53(3H, m), 1.53–1.75(2H, m), 3.25 (3/2H, s), 3.48(3/2H, s), 3.75(3/2H, m), 3.81 (3/2H, m), 3.82–3.87(1H, m), 4.06–4.25(5/2H, m), 4.45–4.59(2H, m), 4.67(1/2H, d, J=13.2Hz), 4.81 (1/2H, m, J=13.2Hz), 4.92(1/2H, d, J=4.4Hz), 6.79–7.53(8H, m) |
| 36 | 0.89–0.95(3H, m), 1.39–1.48(3H, m), 1.58–1.72(2H, m), 2.20(3/2H, s), 2.32(3/2H, s), 3.22(3/2H, s), 3.42(3/2H, s), 3.77(3/2H, s), 3.82(3/2H, s), 3.88–4.92(7H, m), 6.80–7.33(8H, m) |

TABLE 3

Physical properties of the compound in general formula (I)

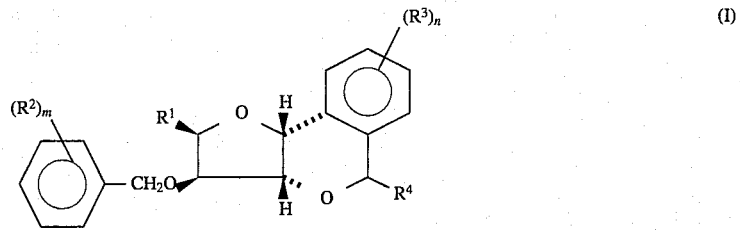

(I)

| Compound No. | Substituents in general formula (I) | | | | Physical properties |
|---|---|---|---|---|---|
| | $R^1$ | $(R^2)_m$ | $(R^3)_n$ | $R^4$ | |
| 1 | $C_2H_5$ | o-F | H | H | NMR (400MHz, $CDCl_3$) δ ppm: 0.90(3H, t, J=7.3Hz), 1.72–1.80(2H, m), 4.04(1H, d, J=2.9Hz), 4.10–4.15 (1H, m), 4.35(1H, d, J=3.7Hz), 4.64(1H, d, J=14.7Hz), 4.65(1H, d, J=12.5Hz), 4.76(1H, d, J=12.5Hz), 4.83 (1H, d, J=14.7Hz), 4.89(1H, d, J=3.7Hz), 7.03–7.52 (8H, m) $[\alpha]_D = -34.7°$ (c=0.94, EtOH) |
| 2 | $C_2H_5$ | o-F | 6-$CH_3$ | H | NMR(400MHz, $CDCl_3$) δ ppm: 0.90(3H, t, J=7.3Hz), 1.72–1.80(2H, m), 2.19(3H, s), 4.05(1H, d, J=2.9Hz), 4.11–4.18(1H, m), 4.29(1H, d, J=3.7Hz), 4.52(1H, d, J=14.7Hz), 4.66(1H, d, J=12.5Hz), 4.82(1H, d, J=12.5 Hz), 4.85(1H, d, J=14.7Hz), 4.88(1H, d, J=3.7Hz), 7.03–7.48(7H, m) |
| 3 | $C_2H_5$ | o-F | 7-$CH_3$ | H | NMR(400MHz, $CDCl_3$) δ ppm: 0.89(3H, t, J=7.3Hz), 1.72–1.79(2H, m), 2.32(3H, s), 4.02(1H, d, J=2.9Hz), 4.09–4.13(1H, m), 4.33(1H, d, J=3.7Hz), 4.60(1H, d, J=13.9Hz), 4.64(1H, d, J=11.7Hz), 4.72(1H, d, J=13.9 Hz), 4.82(1H, d, J=11.7Hz), 4.87(1H, d, J=3.7Hz), 6.86–7.48(7H, m) |
| 4 | $C_2H_5$ | o-F | 8-$CH_3$ | H | NMR(400MHz, $CDCl_3$) δ ppm: 0.89(3H, t, J=7.3Hz), 1.73–1.80(2H, m), 2.34(3H, s), 4.03(1H, d, J=3.7Hz), 4.09–4.15(1H, m), 4.32(1H, d, J=3.7Hz), 4.61(1H, d, J=14.7Hz), 4.65(1H, d, J=12.5Hz), 4.73(1H, d, J=14.7 Hz), 4.82(1H, d, J=12.5Hz), 4.86(1H, d, J=3.7Hz), 6.94–7.48(7H, m) |
| 5 | $C_2H_5$ | o-F | 7-F | H | NMR(400MHz, $CDCl_3$) δ ppm: 0.89(3H, t, J=7.3Hz), 1.71–1.79(2H, m), 4.03(1H, d, J=3.7Hz), 4.09–4.15 (1H, m), 4.32(1H, d, J=2.9Hz), 4.59(1H, d, J=14.7Hz), 4.64(1H, d, J=11.7Hz), 4.73(1H, d, J=14.7Hz), 4.82 (1H, d, J=11.7Hz), 4.85(1H, d, J=2.9Hz), 6.74–7.50 (7H, m) |
| 6 | $C_2H_5$ | o-F | 7-$OCH_3$ | H | NMR(400MHz, $CDCl_3$) δ ppm: 0.89(3H, t, J=7.3Hz), 1.71–1.83(2H, m), 3.79(3H, s), 4.03(1H, d, J=2.9Hz), 4.09–4.15(1H, m), 4.32(1H, d, J=2.9Hz), 4.60–4.77 (3H, m), 4.82(1H, d, J=11.7Hz), 4.86(1H, d, J=2.9Hz), 6.57–7.49(7H, m) |
| 7 | $C_2H_5$ | o-F | 7-OPh | H | NMR(400MHz, $CDCl_3$) δ ppm: 0.90(3H, t, J=7.4Hz), 1.70–1.80(2H, m), 4.04(1H, d, J=3.7Hz), 4.12–4.16 (1H, m), 4.32(1H, d, J=3.7Hz), 4.59(1H, d, J=14.7Hz), 4.64(1H, d, J=12.5Hz), 4.70(1H, d, J=14.7Hz), 4.82 (1H, d, J=12.5Hz), 4.88(1H, d, J=3.7Hz), 6.67–7.48 (12H, m) |
| 8-A | $C_2H_5$ | o-F | H | $CH_3$ | NMR(400MHz, $CDCl_3$) δ ppm: 0.90(3H, t, J=7.3Hz), 1.60(3H, d, J=6.6Hz), 1.73–1.80(2H, m), 4.05(1H, d, J=3.7Hz), 4.12–4.16(1H, m), 4.41(1H, d, J=3.7Hz), 4.65(1H, q, J=6.6Hz), 4.66(1H, d, J=12.5Hz), 4.84 (1H, d, J=12.5Hz), 4.89(1H, d, J=3.7Hz), 7.03–7.52 (8H, m) $[\alpha]_D^{25} = -44.8°$ (c=0.80, EtOH) |
| 8-B | $C_2H_5$ | o-F | H | $CH_3$ | NMR(400MHz, $CDCl_3$) δ ppm: 0.90(3H, t, J=7.3Hz), 1.50(3H, d, J=6.6Hz), 1.76(2H, dq, J=7.3, 7.3Hz), 4.02(1H, d, J=3.7Hz), 4.11(1H, dt, J=3.7, 7.3Hz), 4.56(1H, d, J=3.7Hz), 4.67(1H, d, J=11.7Hz), 4.81 (1H, d, J=11.7Hz), 4.89(1H, d, J=3.7Hz), 5.00(1H, q, J=6.6Hz), 7.03–7.49(8H, m) $[\alpha]_D = -0.2°$ (c=1.54, EtOH) |
| 9 | $C_2H_5$ | o-Cl | H | H | NMR(400MHz, $CDCl_3$) δ ppm: 0.93(3H, t, J=7.3Hz), 1.77–1.85(2H, m), 4.08(1H, d, J=3.0Hz), 4.13–4.18 (1H, m), 4.39(1H, d, J=2.9Hz), 4.65(1H, d, J=14.7Hz), 4.67(1H, d, J=12.5Hz), 4.74(1H, d, J=14.7Hz), 4.86 (1H, d, J=12.5Hz), 4.92(1H, d, J=2.9Hz), 7.05–7.55 (8H, m) |

TABLE 3-continued

Physical properties of the compound in general formula (I)

(I)

| Compound No. | Substituents in general formula (I) | | | | Physical properties |
|---|---|---|---|---|---|
| | $R^1$ | $(R^2)_m$ | $(R^3)_n$ | $R^4$ | |
| 10 | $C_2H_5$ | o-Cl | 6-$CH_3$ | H | NMR(400MHz, $CDCl_3$) δ ppm: 0.93(3H, t, J=7.7Hz), 1.74–1.83(2H, m), 2.17(3H, s), 4.08(1H, d, J=3.7Hz), 4.16–4.21(1H, m), 4.31(1H, d, J=2.9Hz), 4.50(1H, d, J=14.7Hz), 4.68(1H, d, J=12.5Hz), 4.84(1H, d, J=12.5 Hz), 4.85(1H, d, J=14.7Hz), 4.88(1H, d, J=2.9Hz), 7.07–7.54(7H, m) |
| 11 | $C_2H_5$ | H | H | H | NMR(400MHz, $CDCl_3$) δ ppm: 0.90(3H, t, J=7.3Hz), 1.74–1.82(2H, m), 4.04(1H, d, J=2.9Hz), 4.10–4.15 (1H, m), 4.34(1H, d, J=3.7Hz), 4.55(1H, d, J=12.5Hz), 4.64(1H, d, J=14.7Hz), 4.70(1H, d, J=12.5Hz), 4.83 (1H, d, J=14.7Hz), 4.89(1H, t, J=3.7Hz), 7.04–7.50 (9H, m) |
| 12 | $C_2H_5$ | o-$CH_3$ | H | H | NMR(400MHz, $CDCl_3$) δ ppm: 0.90(3H, t, J=7.4Hz), 1.72–1.80(2H, m), 2.35(3H, s), 4.05(1H, d, J=2.9Hz), 4.11–4.18(1H, m), 4.33(1H, d, J=2.9Hz), 4.52(1H, d, J=12.5Hz), 4.64(1H, d, J=14.7Hz), 4.72(1H, d, J=12.5 Hz), 4.84(1H, d, J=14.7Hz), 4.88(1H, d, J=2.9Hz), 7.03–7.52(8H, m) |
| 13 | $C_2H_5$ | o-F | 6-$CH_3$ 8-$CH_3$ | H | NMR(400MHz, $CDCl_3$) δ ppm: 0.90(3H, t, J=7.3Hz), 1.72–1.80(2H, m), 2.15(3H, s), 2.30(3H, s), 4.04(1H, d, J=2.9Hz), 4.13–4.18(1H, m), 4.27(1H, d, J=2.9Hz), 4.48(1H, d, J=14.7Hz), 4.65(1H, d, J=11.7Hz), 4.81 (1H, d, J=11.7Hz), 4.82(1H, d, J=14.7Hz), 4.83(1H, d, J=2.9Hz), 6.91–7.48(6H, m) |
| 14 | $C_2H_5$ | o-F | 7-$CH_3$ 8-$CH_3$ | H | NMR(400MHz, $CDCl_3$) δ ppm: 0.88(3H, t, J=7.3Hz), 1.72–1.79(2H, m), 2.23(3H, s), 2.24(3H, s), 4.02(1H, d, J=3.7Hz), 4.10–4.17(1H, m), 4.31(1H, d, J=2.9Hz), 4.58(1H, d, J=14.7Hz), 4.64(1H, d, J=11.7Hz), 4.69 (1H, d, J=14.7Hz), 4.82(1H, d, J=11.7Hz), 4.85(1H, d, J=2.9Hz), 6.82–7.48(6H, m) |
| 15 | $CH_3$ | H | H | H | NMR(400MHz, $CDCl_3$) δ ppm: 1.34(3H, d, J=6.6Hz), 3.95(1H, d, J=3.7Hz), 4.32(1H, d, J=2.9Hz), 4.38(1H, dq, J=6.6, 3.7Hz), 4.61(1H, d, J=14.7Hz), 4.63(1H, d, J=12.5Hz), 4.75(1H, d, J=14.7Hz), 4.76(1H, d, J=12.5 Hz), 4.91(1H, d, J=2.9Hz), 7.04–7.51(9H, m) |
| 16 | $CH_3$ | o-F | H | H | NMR(400MHz, $CDCl_3$) δ ppm: 1.32(3H, d, J=6.6Hz), 3.97(1H, d, J=3.7Hz), 4.34(1H, d, J=2.9Hz), 4.35–4.43(1H, m), 4.63(1H, d, J=13.9Hz), 4.69(1H, d, J=11.7Hz), 4.75(1H, d, J=13.9Hz), 4.81(1H, d, J=11.7Hz), 4.90(1H, d, J=2.9Hz), 7.03–7.52(8H, m) |
| 17 | $CH_3$ | o-Cl | H | H | NMR(400MHz, $CDCl_3$) δ ppm: 1.32(3H, d, J=6.6Hz), 3.93(1H, d, J=3.7Hz), 4.30(1H, d, J=2.9Hz), 4.38(1H, dq, J=6.6, 3.7Hz), 4.59(1H, d, J=12.5Hz), 4.65(1H, d, J=12.5Hz), 4.71(1H, d, J=12.5Hz), 4.74(1H, d, J=12.5 Hz), 4.90(1H, d, J=3.7Hz), 7.04–7.52(8H, m) |
| 18 | $CH_3$ | o-$CH_3$ | H | H | NMR(400MHz, $CDCl_3$) δ ppm: 1.32(3H, d, J=6.6Hz), 2.37(3H, s), 3.96(1H, d, J=3.7Hz), 4.33(1H, d, J=2.9 Hz), 4.39(1H, dq, J=6.6, 3.7Hz), 4.60(1H, d, J=11.7Hz), 4.63(1H, d, J=14.6Hz), 4.75(1H, d, J=11.7Hz), 4.76 (1H, d, J=14.6Hz), 4.90(1H, d, J=2.9Hz), 7.04–7.51 8H, m) |
| 19 | $CH_3$ | o-$CH_3$ | 6-$CH_3$ | H | NMR(400MHz, $CDCl_3$) δ ppm: 1.32(3H, d, J=6.6Hz), 2.19(3H, s), 2.36(3H, s), 3.97(1H, d, J=3.7Hz), 4.27 (1H, d, J=2.9Hz), 4.43(1H, dq, J=6.6, 3.7Hz), 4.51 (1H, d, J=14.7Hz), 4.60(1H, d, J=11.7Hz), 4.74(1H, d, J=11.7Hz), 4.85(1H, d, J=14.7Hz), 4.88(1H, d, J=3.7Hz), 7.17–7.39(7H, m) |
| 20 | $CH_3$ | o-$CH_3$ | 7-$OCH_3$ | H | NMR(400MHz, $CDCl_3$) δ ppm: 1.30(3H, d, J=6.6Hz), 2.36(3H, s), 3.77(3H, s), 3.95(1H, d, J=3.7Hz), 4.29(1H, d, J=2.9Hz), 4.39(1H, dq, J=6.6, 3.7Hz), 4.59(1H, d, J=14.7Hz), 4.61(1H, d, J=12.5Hz), 4.71(1H, d, J=14.7Hz), 4.73(1H, d, J=12.5Hz), 4.87(1H, d, J=2.9Hz) |

TABLE 3-continued

Physical properties of the compound in general formula (I)

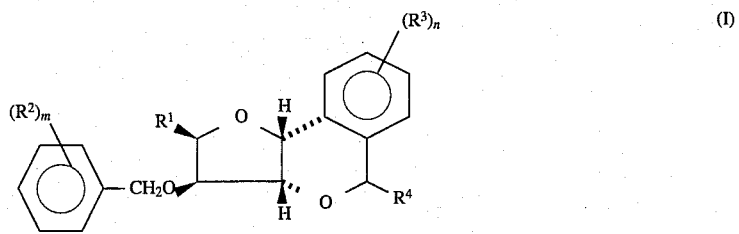

| Compound No. | R¹ | (R²)ₘ | (R³)ₙ | R⁴ | Physical properties |
|---|---|---|---|---|---|
| | | | | | 6.56(1H, d, J=2.2Hz), 6.84(1H, dd, J=2.2, 8.8Hz), 7.16–7.43(5H, m) |
| 21 | $CH_3$ | o-$CH_3$ | 9-$OCH_3$ | H | NMR(400MHz, $CDCl_3$) δ ppm: 1.34(3H, d, J=6.6Hz), 2.36(3H, s), 3.87(3H, s), 3.94(1H, d, J=3.7Hz), 4.22 (1H, d, J=2.9Hz), 4.45(1H, dq, J=6.6, 3.7Hz), 4.59(1H, d, J=14.7Hz), 4.60(1H, d, J=12.5Hz), 4.71(1H, d, J= 14.7Hz), 4.73(1H, d, J=12.5Hz), 5.06(1H, d, J=2.9Hz) 6.64(1H, d, J=8.1Hz), 6.78(1H, d, J=8.1Hz), 7.16– 7.40(5H, m) |
| 22-A | $CH_3$ | H | H | $CH_3$ | NMR(400MHz, $CDCl_3$) δ ppm: 1.33(3H, d, J=6.6Hz), 1.57(3H, d, J=6.6Hz), 3.95(1H, d, J=3.7Hz) 4.37(1H, d, J=3.7Hz), 4.40(1H, dq, J=3.7, 6.6Hz), 4.62(1H, q, J= 6.6Hz), 4.63(1H, d, J=12.5Hz), 4.77(1H, d, J=12.5Hz), 4.90(1H, d, J=3.7Hz), 7.15–7.52(9H, m) |
| 23-A | $CH_3$ | o-F | H | $CH_3$ | NMR(400MHz, $CDCl_3$) δ ppm: 1.32(3H, d, J=6.6Hz), 1.59(3H, d, J=6.6Hz), 3.98(1H, d, J=2.9Hz), 4.40(1H, dq, J=3.7, 6.6Hz), 4.40(1H, d, J=3.7Hz), 4.64(1H, q, J=6.6Hz), 4.69(1H, d, J=12.5Hz), 4.82(1H, d, J= 12.5Hz), 4.90(1H, d, J=3.7Hz), 7.02–7.52(8H, m) |
| 23-B | $CH_3$ | o-F | H | $CH_3$ | NMR(400MHz, $CDCl_3$) δ ppm: 1.31(3H, d, J=6.6Hz), 1.49(3H, d, J=6.6Hz), 3.96(1H, d, J=3.7Hz), 4.38(1H, dq, J=3.7, 6.6Hz), 4.56(1H, d, J=2.9Hz), 4.70(1H, d, J= 11.7Hz), 4.81(1H, d, J=11.7Hz), 4.90(1H, d, J=2.9Hz), 4.99(1H, q, J=6.6Hz), 7.04–7.51(8H, m) |
| 24-A | $CH_3$ | o-Cl | H | $CH_3$ | NMR(400MHz, $CDCl_3$) δ ppm: 1.32(3H, d, J=6.6Hz), 1.57(3H, d, J=5.9Hz), 3.93(1H, d, J=3.7Hz), 4.36(1H, d, J=3.7Hz), 4.39(1H, dq, J=6.6, 3.7Hz), 4.59(1H, d, J= 11.7Hz), 4.62(1H, q, J=5.9Hz), 4.72(1H, d, J=11.7Hz), 4.89(1H, d, J=3.7Hz), 7.15–7.51(8H, m) |
| 24-B | $CH_3$ | o-Cl | H | $CH_3$ | NMR(400MHz, $CDCl_3$) δ ppm: 1.32(3H, d, J=6.6Hz), 1.49(3H, d, J=6.6Hz), 3.91(1H, d, J=3.7Hz), 4.36(1H, dq, J=6.6, 3.7Hz), 4.53(1H, d, J=3.7Hz), 4.58(1H, d, J= 12.5Hz), 4.72(1H, d, J=12.5Hz), 4.90(1H, d, J=3.7Hz), 4.98(1H, q, J=6.6Hz), 7.24–7.28(8H, m) |
| 25 | n-$C_3H_7$ | o-F | H | H | NMR(400MHz, $CDCl_3$) δ ppm: 0.92(3H, t, J=7.3Hz), 1.31–1.48(2H, m), 1.65–1.74(2H, m), 4.01(1H, d, J= 3.7Hz), 4.17–4.21(1H, m), 4.35(1H, d, J=2.9Hz), 4.63 (1H, d, J=14.7Hz), 4.65(1H, d, J=12.5Hz), 4.76(1H, d, J=14.7Hz), 4.82(1H, d, J=12.5Hz), 4.88(1H, d, J=2.9 Hz), 7.01–7.52(8H, m) |
| 26 | n-$C_3H_7$ | o-Cl | H | H | NMR(400MHz, $CDCl_3$) δ ppm: 0.95(3H, t, J=7.3Hz), 1.34–1.50(2H, m), 1.70–1.79(2H, m), 4.05(1H, d, J= 3.7Hz), 4.20–4.24(1H, m), 4.39(1H, d, J=2.9Hz), 4.64 (1H, d, J=14.7Hz), 4.68(1H, d, J=12.5Hz), 4.75(1H, d, J=14.7Hz), 4.86(1H, d, J=12.5Hz), 4.91(1H, d, J=2.9 Hz), 7.04–7.55(8H, m) |
| 27 | $C_2H_5$ | o-F | 8-isoPr | H | NMR(400MHz, $CDCl_3$) δ ppm: 0.90(3H, t, J=7.3Hz), 1.18–1.25(6H, m), 1.73–1.81(2H, m), 2.87–2.94(1H, m), 4.03(1H, d, J=3.7Hz), 4.12–4.17(1H, m), 4.31(1H, d, J=3.7Hz), 4.62(1H, d, J=14.7Hz), 4.65(1H, d, J= 11.7Hz), 4.75(1H, d, J=14.7Hz), 4.81(1H, d, J=11.7Hz), 4.88(1H, d, J=3.7Hz), 6.97–7.48(7H, m) |
| 28 | $C_2H_5$ | o-F | 6-$CH_2Br$ | H | NMR(400MHz, $CDCl_3$) δ ppm: 0.90(3H, t, J=7.3Hz), 1.72–1.80(2H, m), 4.06(1H, d, J=2.9Hz), 4.11–4.16(1H, m), 4.35(1H, d, J=3.7Hz), 4.36(1H, d, J=11.0Hz), 4.48(1H, d, J=11.0Hz), 4.64(1H, d, J=15.4Hz), 4.66(1H, d, J=11.7Hz), 4.82(1H, d, J=11.7Hz), 4.88(1H, d, J=3.7Hz), 5.03(1H, d, J=15.4Hz), 7.04–7.51(7H, m) |
| 29 | $C_2H_5$ | o-F | 7-Cl | H | NMR(400MHz, $CDCl_3$) δ ppm: 0.89(3H, t, J=7.3Hz), 1.73(2H, dq, J=7.3, 7.3Hz), 4.02(1H, d, J=3.7Hz), 4.08(1H, dt, J=7.3, 3.7), 4.32(1H, d, J=3.7Hz), 4.57 (1H, d, J=14.7Hz), 4.63(1H, d, J=11.7Hz), 4.62(1H, d, J= |

TABLE 3-continued

Physical properties of the compound in general formula (I)

$$\text{(structure with } (R^2)_m \text{ phenyl-CH}_2\text{O-, } R^1, \text{ O, H, } (R^3)_n \text{ phenyl, } O-R^4\text{)} \quad (I)$$

| Compound No. | R¹ | (R²)ₘ | (R³)ₙ | R⁴ | Physical properties |
|---|---|---|---|---|---|
| | | | | | 14.7Hz), 4.79(1H, d, J=11.7Hz), 4.83(1H, d, J=3.7Hz), 7.02–7.46(7H, m) |
| 30 | C₂H₅ | o-F | 7-Br | H | NMR(400MHz, CDCl₃) δ ppm: 0.89(3H, t, J=7.3Hz), 1.70–1.77(2H, m), 4.02(1H, d, J=3.7Hz), 4.06–4.10 (1H, m), 4.32(1H, d, J=3.7Hz), 4.58(1H, d, J=14.7Hz), 4.63(1H, d, J=11.7Hz), 4.71(1H, d, J=14.7Hz), 4.80 (1H, d, J=11.7Hz), 4.82(1H, d, J=3.7Hz), 7.03–7.47 (7H, m) |
| 31-A | C₂H₅ | o-F | 7-OCH₃ | CH₃ | NMR(400MHz, CDCl₃) δ ppm: 0.90(3H, t, J=7.3Hz), 1.58(3H, d, J=6.6Hz), 1.75(2H, dq, J=7.3, 7.3Hz), 3.80(3H, s), 4.03(1H, d, J=3.7Hz), 4.14(1H, dt, J= 3.7, 7.3Hz), 4.36(1H, d, J=2.9Hz), 4.61(1H, q, J=6.6 Hz), 4.65(1H, d, J=11.7Hz), 4.81(1H, d, J=11.7Hz), 4.85(1H, d, J=2.9Hz), 6.69(1H, d, J=2.2Hz), 6.85(1H, dd, J=2.2, 8.8Hz), 7.02–7.49(5H, m) |
| 32-B | C₂H₅ | o-F | 6-CH₃ | CH₃ | NMR(400MHz, CDCl₃) δ ppm: 0.94(3H, t, J=7.3Hz), 1.52(3H, d, J=6.6Hz), 1.77(2H, dq, J=7.3, 7.3Hz), 2.28(3H, S), 4.05(1H, d, J=3.7Hz), 4.20(1H, d, J=2.2 Hz), 4.34(1H, dt, J=3.7, 7.3Hz), 4.62(1H, d, J=11.7Hz), 4.76(1H, d, J=11.7Hz), 4.85(1H, d, J=2.2Hz), 5.00 (1H, q, J=6.6Hz), 7.01–7.46(7H, m) |
| 33-A | C₂H₅ | o-F | 7-Cl | CH₃ | NMR(400MHz, CDCl₃) δ ppm: 0.90(3H, t, J=7.3Hz), 1.58(3H, d, J=6.6Hz), 1.75(2H, dq, J=7.3, 7.3Hz), 4.03(1H, d, J=3.7Hz), 4.10(1H, dt, J=3.7, 7.3Hz), 4.39(1H, d, J=3.7Hz), 4.58(1H, q, J=6.6Hz), 4.65 (1H, d, J=12.5Hz), 4.82(1H, d, J=12.5Hz), 4.84(1H, d, J=3.7Hz), 7.03–7.48(7H, m) |
| 33-B | C₂H₅ | o-F | 7-Cl | CH₃ | NMR(400MHz, CDCl₃) δ ppm: 0.89(3H, t, J=7.3Hz), 1.49(3H, d, J=6.6Hz), 1.74(2H, dq, J=7.3, 7.3Hz), 4.00(1H, d, J=3.7Hz), 4.07(1H, dt, J=3.7, 7.3Hz), 4.53(1H, d, J=3.7Hz), 4.66(1H, d, J=11.7Hz), 4.80 (1H, d, J=11.7Hz), 4.83(1H, d, J=3.7Hz), 4.95(1H, q, J= 6.6Hz), 7.04–7.48(7H, m) |
| 34 | C₂H₅ | o-Cl | 8-C₂H₅ | H | NMR(400MHz, CDCl₃) δ ppm: 0.93(3H, t, J=7.3Hz), 1.24(3H, t, J=7.3Hz), 1.77–1.85(2H, m), 2.58–2.68 (2H, m), 4.08(1H, d, J=2.9Hz), 4.15–4.20(1H, m), 4.35 (1H, d, J=3.7Hz), 4.63(1H, d, J=14.7Hz), 4.67(1H, d, J= 12.5Hz), 4.75(1H, d, J=14.7Hz), 4.86(1H, d, J=12.5Hz), 4.90(1H, d, J=3.7Hz), 6.97–7.55(7H, m) |
| 35 | C₂H₅ | o-Cl | 7-OCH₃ | H | NMR(400MHz, CDCl₃) δ ppm: 0.92(3H, t, J=7.3Hz), 1.77–1.82(2H, m), 3.79(3H, s), 4.07(1H, d, J=2.9Hz), 4.11–4.18(1H, m), 4.35(1H, d, J=2.9Hz), 4.63(1H, d, J= 14.7Hz), 4.66(1H, d, J=13.2Hz), 4.74(1H, d, J=14.7 Hz), 4.86(1H, d, J=13.2Hz), 4.89(1H, d, J=2.9Hz), 6.58(1H, d, J=2.9Hz), 6.86(1H, dd, J=2.9, 8.8Hz), 7.22–7.55(5H, m) |
| 36 | C₂H₅ | o-Cl | 9-OCH₃ | H | NMR(400MHz, CDCl₃) δ ppm: 0.92(3H, t, J=7.3Hz), 1.80–1.88(2H, m), 3.88(3H, s), 4.08(1H, d, J=2.9Hz), 4.19–4.24(1H, m), 4.29(1H, d, J=2.9Hz), 4.65(1H, d, J= 14.7H), 4.67(1H, d, J=13.2Hz), 4.80(1H, d, J=14.7 Hz), 4.84(1H, d, J=13.2Hz), 5.07(1H, d, J=2.9Hz), 6.65(1H, d, J=8.1Hz), 6.80(1H, d, J=8.1Hz), 7.22–7.57(5H, m) |
| 37-A | C₂H₅ | o-Cl | H | CH₃ | NMR(400MHz, CDCl₃) δ ppm: 0.93(3H, t, J=7.3Hz), 1.61(3H, d, J=6.6Hz), 1.79–1.83(2H, m), 4.09(1H, d, J= 2.9Hz), 4.15–4.19(1H, m), 4.44(1H, d, J=3.7Hz), 4.66(1H, q, J=6.6Hz), 4.67(1H, d, J=12.5Hz), 4.87 (1H, d, J=12.5Hz), 4.91(1H, d, J=3.7Hz), 7.17–7.56 (8H, m) |
| 37-B | C₂H₅ | o-Cl | H | CH₃ | NMR(400MHz, CDCl₃) δ ppm: 0.92(3H, t, J=7.3Hz), 1.51(3H, d, J=6.6Hz), 1.75–1.81(2H, m), 4.05(1H, d, J= 3.7Hz), 4.11–4.15(1H, m), 4.60(1H, d, J=3.7Hz), |

TABLE 3-continued

Physical properties of the compound in general formula (I)

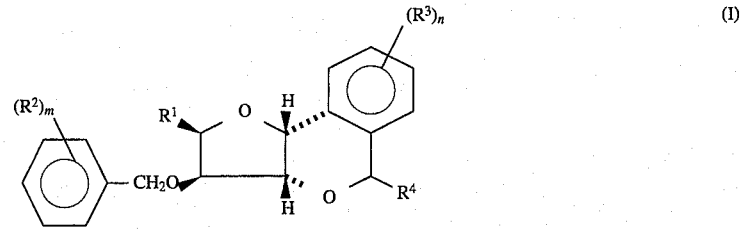

(I)

| Compound No. | Substituents in general formula (I) | | | | Physical properties |
|---|---|---|---|---|---|
| | $R^1$ | $(R^2)_m$ | $(R^3)_n$ | $R^4$ | |
| | | | | | 4.72(1H, d, J=12.5Hz), 4.85(1H, d, J=12.5Hz), 4.91 (1H, d, J=3.7Hz), 5.01(1H, q, J=6.6Hz), 7.03–7.56(8H, m) |
| 38-A | $C_2H_5$ | o-Cl | 7-$OCH_3$ | $CH_3$ | NMR(400MHz, $CDCl_3$) δ ppm: 0.93(3H, t, J=7.3Hz), 1.59(3H, d, J=6.6Hz), 1.78–1.82(2H, m), 3.81(3H, s), 4.08(1H, d, J=3.7Hz), 4.17(1H, dt, J=7.3, 3.7Hz), 4.40(1H, d, J=2.9Hz), 4.64(1H, q, J=6.6Hz), 4.67(1H, d, J=11.7Hz), 4.86(1H, d, J=11.7Hz), 4.88(1H, d, J=2.9Hz), 6.70(1H, d, J=2.2Hz), 6.85(1H, dd, J=8.1, 2.2Hz), 7.22–7.56(5H, m) melting point 69–70.5° C. |
| 38-B | $C_2H_5$ | o-Cl | 7-$OCH_3$ | $CH_3$ | NMR(400MHz, $CDCl_3$) δ ppm: 0.91(3H, t, J=7.3Hz), 1.51(3H, d, J=6.6Hz), 1.74–1.81(2H, m), 3.79(3H, s), 4.04(1H, d, J=3.7Hz), 4.13(1H, dt, J=7.3, 3.7Hz), 4.56(1H, d, J=2.9Hz), 4.68(1H, d, J=12.5Hz), 4.85 (1H, d, J=12.5Hz), 4.88(1H, d, J=2.9Hz), 4.97(1H, q, J=6.6Hz), 6.56(1H, d, J=2.2Hz), 6.84(1H, dd, J=8.1, 2.2Hz), 7.22–7.56(5H, m) |
| 39-A | $C_2H_5$ | o-Cl | 9-$OCH_3$ | $CH_3$ | NMR(400MHz, $CDCl_3$) δ ppm: 0.93(3H, t, J=7.3Hz), 1.59(3H, d, J=6.6Hz), 1.81–1.85(2H, m), 3.89(3H, s), 4.07(1H, d, J=3.7Hz), 4.21–4.26(1H, m), 4.35(1H, d, J=2.9Hz), 4.70(1H, d, J=11.7Hz), 4.72(1H, q, J=6.6Hz) 4.83(1H, d, J=11.7Hz), 5.06(1H, d, J=2.9Hz), 6.65 (1H, d, J=8.1Hz), 6.79(1H, d, J=8.1Hz), 7.35–7.57(5H, m) |
| 39-B | $C_2H_5$ | o-Cl | 9-$OCH_3$ | $CH_3$ | NMR(400MHz, $CDCl_3$) δ ppm: 0.91(3H, t, J=7.3Hz), 1.49(3H, d, J=6.6Hz), 1.77–1.87(2H, m), 3.88(3H, s), 4.05(1H, d, J=3.7Hz), 4.17–4.22(1H, m), 4.51(1H, d, J=2.9Hz), 4.69(1H, d, J=12.5Hz), 4.84(1H, d, J=12.5Hz), 5.01(1H, q, J=6.6Hz), 5.10(1H, d, J=2.9Hz), 6.65 (1H, d, J=8.1Hz), 6.78(1H, d, J=8.1Hz), 7.22–7.58(5H, m) |
| 40-A | $C_2H_5$ | o-Cl | H | $C_2H_5$ | NMR(400MHz, $CDCl_3$) δ ppm: 0.94(3H, t, J=7.3Hz), 0.98(3H, t, J=7.3Hz), 1.71–1.91(3H, m), 2.11–2.17 (1H, m), 4.08(1H, d, J=2.9Hz), 4.18(1H, dt, J=2.9, 7.3 Hz), 4.39(1H, d, J=3.7Hz), 4.55(1H, dd, J=3.7, 7.3Hz) 4.68(1H, d, J=12.5Hz), 4.85(1H, d, J=12.5Hz), 4.89 (1H, d, J=3.7Hz), 7.16–7.56(8H, m) |
| 40-B | $C_2H_5$ | o-Cl | H | $C_2H_5$ | NMR(400MHz, $CDCl_3$) δ ppm: 0.91(3H, t, J=7.3Hz), 1.12(3H, t, J=7.3Hz), 1.63–1.70(1H, m), 1.75–1.88 (3H, m), 4.05(1H, d, J=3.7Hz), 4.11(1H, dt, J=3.7, 7.3 Hz), 4.52(1H, d, J=3.7Hz), 4.65(1H, dd, J=3.7, 10.6Hz), 4.71(1H, d, J=12.5Hz), 4.82(1H, d, J=12.5Hz), 4.89 (1H, d, J=3.7Hz), 7.02–7.56(8H, m) |
| 41-A | $C_2H_5$ | H | H | $C_2H_5$ | NMR(400MHz, $CDCl_3$) δ ppm: 0.91(3H, t, J=7.3Hz), 0.96(3H, t, J=7.3Hz), 1.75–2.15(4H, m), 4.02(1H, d, J=2.9Hz), 4.14(1H, dt, J=7.3, 2.9Hz), 4.33(1H, d, J=2.9Hz), 4.53(1H, dd, J=6.6, 2.9Hz), 4.61(1H, d, J=11.7Hz), 4.76(1H, d, J=11.7Hz), 4.87(1H, d, J=2.9Hz) 7.15–7.52(9H, m) |
| 42 | $C_2H_5$ | H | 7-$OCH_3$ | H | NMR(400MHz, $CDCl_3$) δ ppm: 0.90(3H, t, J=7.3Hz), 1.77(2H, dq, J=7.3, 7.3Hz), 3.79(3H, s), 4.00(1H, d, J=3.7Hz), 4.11(1H, dt, J=7.3, 3.7Hz), 4.28(1H, d, J=2.9Hz), 4.59(1H, d, J=11.7Hz), 4.60(1H, d, J=16.1Hz) 4.71(1H, d, J=16.1Hz), 4.74(1H, d, J=11.7Hz), 4.86 (1H, d, J=2.9Hz), 6.56(1H, d, J=2.2Hz), 6.85(1H, dd, J=8.1, 2.2Hz), 7.291–7.44(6H, m) |
| 43 | $C_2H_5$ | H | 9-$OCH_3$ | H | NMR(400MHz, $CDCl_3$) δ ppm: 0.89(3H, t, J=7.3Hz), 1.82(2H, dq, J=7.3, 6.6Hz), 3.87(3H, s), 4.01(1H, d, J=3.7Hz), 4.12(1H, dt, J=6.6, 3.7Hz), 4.21(1H, d J=2.9Hz), 4.59(1H, d, J=11.7Hz), 4.61(1H, d, J=16.1Hz) 4.74(1H, d, J=11.7Hz), 4.77(1H, d, J=16.1Hz), 5.05 |

TABLE 3-continued

Physical properties of the compound in general formula (I)

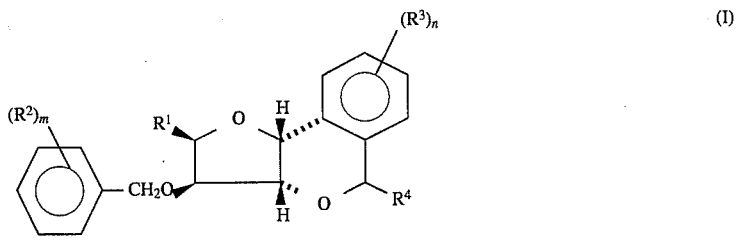

(I)

| Compound No. | Substituents in general formula (I) | | | | Physical properties |
|---|---|---|---|---|---|
| | $R^1$ | $(R^2)_m$ | $(R^3)_n$ | $R^4$ | |
| | | | | | (1H, d, J=2.9Hz), 6.63(1H, d, J=8.1Hz), 6.78(1H, d, J=8.1Hz), 7.21–7.40(6H, m) |
| 44-A | $C_2H_5$ | H | H | $CH_3$ | NMR(400MHz, CDCl$_3$) δ ppm: 0.90(3H, t, J=7.3Hz), 1.57(3H, d, J=6.6Hz), 1.74–1.82(2H, m), 4.02(1H, d, J=2.9Hz), 4.10–4.15(1H, m), 4.37(1H, d, J=3.6Hz), 4.60(1H, d, J=11.7Hz), 4.62(1H, q, J=6.6Hz), 4.76 (1H, d, J=11.7Hz), 4.88(1H, d, J=3.6Hz), 7.15–7.52 (9H, m) |
| 44-B | $C_2H_5$ | H | H | $CH_3$ | NMR(400MHz, CDCl$_3$) δ ppm: 0.90(3H, t, J=7.3Hz), 1.48(3H, d, J=6.6Hz), 1.75–1.79(2H, m), 3.99(1H, d, J=4.4Hz), 4.05–4.13(1H, m), 4.51(1H, d, J=2.9Hz), 4.61(1H, d, J=11.7Hz), 4.74(1H, d, J=11.7Hz), 4.88 (1H, d, J=2.9Hz), 4.98(1H, q, J=6.6Hz), 7.02–7.48(9H, m) |
| 45-A | $C_2H_5$ | H | 7-$OCH_3$ | $CH_3$ | NMR(400MHz, CDCl$_3$) δ ppm: 0.89(3H, t, J=7.3Hz), 1.56(3H, d, J=6.6Hz), 1.73–1.79(2H, m), 3.79(3H, s), 4.00(1H, d, J=2.9Hz), 4.10–4.15(1H, m), 4.31(1H, d, J=2.9Hz), 4.59(1H, d, J=11.7Hz), 4.60(1H, q, J=6.6Hz) 4.75(1H, d, J=11.7Hz), 4.86(1H, d, J=2.9Hz), 6.68 (1H, d, J=2.2Hz), 6.83(1H, dd, J=8.8, 2.2Hz), 7.25–7.44(6H, m) |
| 46-A | $C_2H_5$ | H | 9-$OCH_3$ | $CH_3$ | NMR(400MHz, CDCl$_3$) δ ppm: 0.89(3H, t, J=7.3Hz), 1.57(3H, d, J=6.6Hz), 1.78–1.85(2H, m), 3.87(3H, s) 4.01(1H, d, J=2.9Hz), 4.18–4.22(1H, m), 4.23(1H, d, J=2.9Hz), 4.58(1H, d, J=12.5Hz), 4.65(1H, q, J=6.6Hz) 4.74(1H, d, J=12.5Hz), 5.04(1H, d, J=2.9Hz), 6.75–7.37(8H, m) |
| 46-B | $C_2H_5$ | H | 9-$OCH_3$ | $CH_3$ | NMR(400MHz, CDCl$_3$) δ ppm: 0.88(3H, t, J=7.3Hz), 1.45(3H, d, J=6.6Hz), 1.77–1.84(2H, m), 3.86(3H, s), 3.98(1H, d, J=3.7Hz), 4.13–4.17(1H, m), 4.41(1H, d, J=2.9Hz), 4.60(1H, d, J=11.7Hz), 4.72(1H, d, J=11.7Hz), 4.98(1H, q, J=6.6Hz), 5.07(1H, d, J=2.9Hz), 6.63 (1H, d, J=7.3Hz), 6.77(1H, d, J=7.3Hz), 7.20–7.40(6H, m) |
| 47 | $C_2H_5$ | o-$CH_3$ | 6-$CH_3$ | H | NMR(400MHz, CDCl$_3$) δ ppm: 0.88(3H, t, J=7.3Hz), 1.76(2H, dq, J=7.3, 7.3Hz), 2.18(3H, s), 2.36(3H, s), 4.03(1H, d, J=3.7Hz), 4.15(1H, dt, J=7.3, 3.7Hz), 4.26(1H, d, J=2.9Hz), 4.50(1h, d, J=15.4Hz), 4.57 (1H, d, J=11.7Hz), 4.74(1H, d, J=11.7Hz), 4.84(1H, d, J=15.7Hz), 4.86(1H, d, J=2.9Hz), 7.17–7.27(7H, m) |
| 48-A | $C_2H_5$ | o-$CH_3$ | H | $CH_3$ | NMR(400MHz, CDCl$_3$) δ ppm: 0.87(3H, t, J=7.3Hz), 1.59(3H, d, J=6.6Hz), 1.72–1.80(2H, m), 2.36(3H, s), 4.02(1H, d, J=3.6Hz), 4.09–4.15(1H, m), 4.38(1H, d, J=3.6Hz), 4.56(1H, d, J=11.7Hz), 4.64(1H, q, J=6.6Hz), 4.76(1H, d, J=11.7Hz), 4.87(1H, d, J=3.6Hz), 7.13–7.52(8H, m) |
| 49-A | $C_2H_5$ | o-$CH_3$ | 7-$OCH_3$ | $CH_3$ | NMR(400MHz, CDCl$_3$) δ ppm: 0.87(3H, t, J=7.3Hz), 1.58(3H, d, J=6.6Hz), 1.71–1.78(2H, m), 2.36(3H, s), 3.80(3H, s), 4.02(1H, d, J=3.7Hz), 4.12(1H, dt, J=7.3, 3.7Hz), 4.34(1H, d, J=2.9Hz), 4.56(1H, d, J=11.7 Hz), 4.61(1H, q, J=6.6Hz), 4.76(1H, d, J=11.7Hz), 4.85(1H, d, J=2.9Hz), 6.69(1H, d, J=2.2Hz), 6.85(1H, dd, J=8.1, 2.2Hz), 7.16–7.44(5H, m) melting point 84–85° C. |
| 49-B | $C_2H_5$ | o-$CH_3$ | 7-$OCH_3$ | $CH_3$ | NMR(400MHz, CDCl$_3$) δ ppm: 0.86(3H, t, J=7.3Hz), 1.47(3H, d, J=6.6Hz), 1.74(2H, dq, J=7.3, 7.3Hz), 2.37(3H, s), 3.79(3H, s), 3.99(1H, d, J=.37Hz), 4.10 (1H dt, J=7.3, 3.7Hz), 4.48(1H, d, J=2.9Hz), 4.56 (1H, d, J=11.7Hz), 4.73(1H, d, J=11.7Hz), 4.85(1H, d, J=2.9Hz), 4.95(1H, q, J=6.6Hz), 6.55(1H, d, J=2.2 Hz), 6.83(1H, dd, J=8.1, 2.2Hz), 7.16–7.44(5H, m) |
| 50-A | $C_2H_5$ | o-$CH_3$ | 9-$OCH_3$ | $CH_3$ | NMR(400MHz, CDCl$_3$) δ ppm: 0.87(3H, t, J=7.3Hz), |

TABLE 3-continued

Physical properties of the compound in general formula (I)

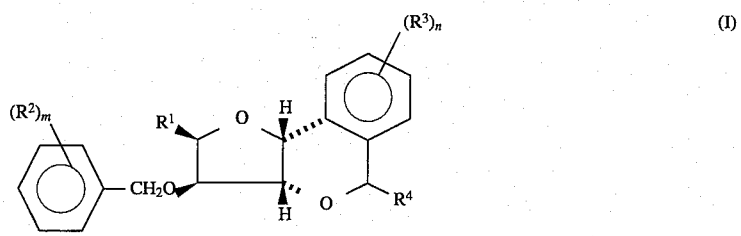

| Compound No. | Substituents in general formula (I) | | | | Physical properties |
|---|---|---|---|---|---|
| | $R^1$ | $(R^2)_m$ | $(R^3)_n$ | $R^4$ | |
| | | | | | 1.57(3H, d, J=6.6Hz), 1.81(2H, dq, J=7.3, 7.3Hz), 2.36(3H, s), 3.87(3H, s), 4.02(1H, d, J=3.7Hz), 4.21 (1H, dt, J=7.3, 3.7Hz), 4.27(1H, d, J=2.9Hz), 4.59 (1H, d, J=11.7Hz), 4.67(1H, q, J=6.6Hz), 4.73(1H, d, J=11.7Hz), 5.03(1H, d, J=2.9Hz), 6.63(1H, d, J=8.1 Hz), 6.76(1H, d, J=8.1Hz), 7.29–7.40(5H, m) |
| 50-B | $C_2H_5$ | o-$CH_3$ | 9-$OCH_3$ | $CH_3$ | NMR(400MHz, $CDCl_3$) δ ppm: 0.86(3H, t, J=7.3Hz), 1.45(3H, d, J=6.6Hz), 1.79(2H, dq, J=7.3, 6.6Hz), 2.37(3H, s), 3.86(3H, s), 3.99(1H, d, J=3.7Hz), 4.14 (1H, dt, J=6.6, 3.7Hz), 4.41(1H, d, J=2.9Hz), 4.59(1H, d, J=11.7Hz), 4.71(1H, d, J=11.7Hz), 4.98(1H, q, J= 6.6Hz), 5.07(1H, d, J=2.9Hz), 6.63(1H, d, J=8.1Hz), 6.76(1H, d, J=8.1Hz), 7.15–7.40(5H, m) |
| 51 | $C_2H_5$ | o-$CH_3$ | 7-$OCH_3$ | H | NMR(400MHz, $CDCl_3$) δ ppm: 0.86(3H, t, J=7.3Hz), 1.71–1.76(2H, m), 2.36(3H, s), 3.78(3H, s), 4.01(1H, d, J=3.6Hz), 4.09–4.14(1H, m), 4.29(1H, d, J=2.9Hz), 4.55(1H, d, J=11.7Hz), 4.61(1H, d, J=14.7Hz), 4.72 (1H, d, J=14.7Hz), 4.74(1H, d, J=11.7Hz), 4.86(1H, d, J= 2.9Hz), 6.56(1H, d, J=2.2Hz), 6.84(1H, dd, J=7.9, 2.2Hz), 7.16–7.43(5H, m) $[\alpha]_D^{25} = -57.1°$ (c=0.81, EtOH) |
| 52 | $C_2H_5$ | o-$CF_3$ | H | H | NMR(400MHz, $CDCl_3$) δ ppm: 0.95(3H, t, J=7.3Hz), 1.77–1.83(2H, m), 4.07(1H, d, J=3.7Hz), 4.16–4.18 (1H, m), 4.36(1H, d, J=3.7Hz), 4.65(1H, d, J=14.7Hz), 4.76(1H, d, J=11.0Hz), 4.77(1H, d, J=14.7Hz), 4.90 (1H, d, J=3.7Hz), 4.95(1H, d, J=11.0Hz), 7.06(1H, d, J= 6.6Hz), 7.25–7.59(5H, m), 7.65(1H, d, J=8.1Hz), 7.75 (1H, d, J=8.1Hz) |
| 53 | $C_2H_5$ | m-F | H | H | NMR(400MHz, $CDCl_3$) δ ppm: 0.92(3H, t, J=7.7Hz), 1.77–1.80(2H, m), 4.01(1H, d, J=3.7Hz), 4.11–4.16 (1H, m), 4.32(1H, d, J=3.7Hz), 4.59(1H, d, J=11.7Hz), 4.62(1H, d, J=14.7Hz), 4.75(1H, d, J=14.7Hz), 4.76 (1H, d, J=11.7Hz), 4.89(1H, d, J=3.7Hz), 6.95–7.30 (7H, m), 7.52(1H, d, J=7.3Hz) |
| 54 | $C_2H_5$ | p-F | H | H | NMR(400MHz, $CDCl_3$) δ ppm: 0.89(3H, t, J=7.3Hz), 1.72–1.79(2H, m), 4.00(1H, d J=3.7Hz), 4.08–4.12 (1H, m), 4.30(1H, d, J=3.7Hz), 4.55(1H, d, J=11.7Hz), 4.62(1H, d, J=14.7Hz), 4.72(1H, d, J=11.7Hz), 4.75 (1H, d, J=14.7Hz), 4.88(1H, d, J=3.7Hz), 7.02–7.36 (7H, m), 7.51(1H, d, J=7.3Hz) |
| 55 | $C_2H_5$ | m-$CH_3$ | H | H | NMR(400MHz, $CDCl_3$) δ ppm: 0.90(3Ht, J=7.3Hz), 1.74–1.82(2H, m), 2.36(3H, S), 4.00(1H, d, J=3.6Hz), 4.08–4.12(1H, m), 4.31(1H, d, J=3.7Hz), 4.55(1H, d, J= 11.7Hz), 4.62(1H, d, J=14.7Hz), 4.71(1H, d, J=11.7 Hz), 4.75(1H, d, J=14.7Hz), 4.89(1H, d, J=3.7Hz), 7.04–8.12(8H, m) |
| 56 | $C_2H_5$ | p-$CH_3$ | H | H | NMR(400MHz, $CDCl_3$) δ ppm: 0.89(3H, t, J=7.3Hz), 1.72–1.80(2H, m), 2.34(3H, S), 3.99(1H, d, J=3.7Hz), 4.07–4.12(1H, m), 4.29(1H, d, J=3.7Hz), 4.55(1H, d, J= 11.7Hz), 4.61(1H, d, J=14.7Hz), 4.70(1H, d, J=11.7Hz), 4.74(1H, d, J=14.7Hz), 4.89(1H, d, J=3.7Hz), 7.01–8.12(8H, m) |
| 57 | $C_2H_5$ | 3-F 5-F | H | H | NMR(400MHz, $CDCl_3$) δ ppm: 0.94(3H, t, J=7.7Hz), 1.75–1.82(2H, m), 4.00(1H, d, J=3.7Hz), 4.11–4.15 (1H, m), 4.32(1H, d, J=3.6Hz), 4.57(1H, d, J=12.2Hz), 4.62(1H, d, J=13.9Hz), 4.74(1H, d, J=12.2Hz), 4.75 (1H, d, J=13.9Hz), 4.89(1H, d, J=3.6Hz), 6.70–8.15 (7H, m) |
| 58 | $C_2H_5$ | 2-F 6-F | H | H | NMR(400MHz, $CDCl_3$) δ ppm: 0.85(3H, t, J=7.3Hz), 1.65–1.72(2H, m), 4.02(1H, d, J=2.9Hz), 4.07–4.13 (1H, m), 4.37(1H, d, J=3.7Hz), 4.66(1H, d, J=14.7Hz), 4.68(1H, d, J=11.0Hz), 4.77(1H, d, J=14.7Hz), 4.80 |

TABLE 3-continued

Physical properties of the compound in general formula (I)

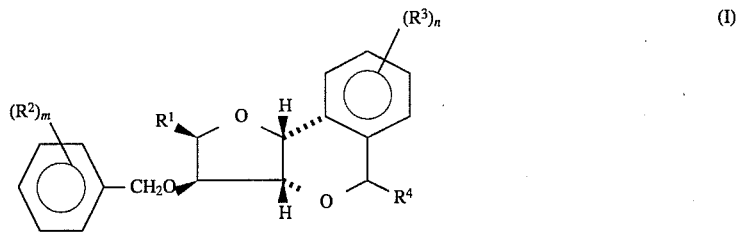

| Compound No. | Substituents in general formula (I) | | | | Physical properties |
|---|---|---|---|---|---|
| | $R^1$ | $(R^2)_m$ | $(R^3)_n$ | $R^4$ | |
| | | | | | (1H, d, J=11.0Hz), 4.87(1H, d, J=3.7Hz), 6.87–7.51 (7H, m) |
| 59 | $C_2H_5$ | 2-$CH_3$ 4-$CH_3$ | H | H | NMR(400MHz, $CDCl_3$) δ ppm: 0.85(3H, t, J=7.3Hz), 1.70–1.76(2H, m), 2.31(3H, S), 2.33(3H, S), 4.00(1H, d, J=3.7Hz), 4.09–4.11(1H, m), 4.31(1H, d, J=3.7Hz), 4.53(1H, d, J=11.7Hz), 4.63(1H, d, J=14.3Hz), 4.71 (1H, d, J=11.7Hz), 4.76(1H, d, J=14.3Hz), 4.87(1H, d, J=3.7Hz), 6.99–7.51(7H, m) |
| 60 | $C_2H_5$ | m-$OCH_3$ | H | H | NMR(400MHz, $CDCl_3$) δ ppm: 0.91(3H, t, J=7.3Hz), 1.75–1.82(2H, m), 3.81(3H, S), 4.02(1H, d, J=3.7Hz), 4.09–4.13(1H, m), 4.31(1H, d, J=3.7Hz), 4.57(1H, d, J=11.7Hz), 4.62(1H, d, J=14.7Hz), 4.73(1H, d, J=11.7 Hz), 4.74(1H, d, J=14.7Hz), 4.90(1H, d, J=3.7Hz), 6.83(1H, d, J=7.3Hz), 6.94–6.99(2H, m), 7.04(1H, d, J=7.3Hz), 7.24–8.12(3H, m) |
| 61 | $C_2H_5$ | 2-F 6-Cl | H | H | NMR(400MHz, $CDCl_3$) δ ppm: 0.86(3H, t, J=7.3Hz), 1.69(2H, dq, J=7.3, 7.3Hz), 4.02(1H, d, J=3.7Hz), 4.12(1H, dt, J=3.7, 7.3Hz), 4.40(1H, d, J=3.7Hz), 4.65–4.88(4H, m), 4.88(1H, d, J=3.7Hz), 7.00–7.51 (7H, m) |
| 62 | $C_2H_5$ | o-F | 7-I | H | NMR(400MHz, $CDCl_3$) δ ppm: 0.89(3H, t, J=7.3Hz), 1.70–1.77(2H, m), 4.02(1H, d, J=3.7Hz), 4.06–4.10 (1H, m), 4.32(1H, d, J=3.7Hz), 4.59(1H, d, J=14.7Hz), 4.63(1H, d, J=11.7Hz), 4.75(1H, d, J=14.7Hz), 4.80 (1H, d, J=11.7Hz), 4.83(1H, d, J=3.7Hz), 7.08–7.59 (7H, m) |
| 63 | $C_2H_5$ | o-F | 7-$CF_3$ | H | NMR(400MHz, $CDCl_3$) δ ppm: 0.89(3H, t, J=7.3Hz), 1.71–1.79(2H, m), 4.02(1H, d, J=3.7Hz), 4.07–4.12 (1H, m), 4.33(1H, d, J=3.7Hz), 4.61(1H, d, J=14.7Hz), 4.65(1H, d, J=11.7Hz), 4.77(1H, d, J=14.7Hz), 4.82 (1H, d, J=11.7Hz), 4.85(1H, d, J=3.7Hz), 7.08–7.55 (7H, m) |
| 64 | $C_2H_5$ | o-Cl | 7-$CH_2Ph$ | H | NMR(400MHz, $CDCl_3$) δ ppm: 0.90(3H, t, J=7.3Hz), 1.72–1.80(2H, m), 4.06(1H, d, J=2.9Hz), 4.11–4.16 (1H, m), 44.35(1H, d, J=3.7Hz), 4.64(1H, d, J=15.4Hz), 4.66(1H, d, J=11.7Hz), 4.82(1H, d, J=15.4Hz), 4.86 (1H, d, J=11.7Hz), 4.90(1H, d, J=3.7Hz), 4.89(2H, m), 6.64–7.57(12H, m) |
| 65 | $C_2H_5$ | o-Cl | 7-$OCH_3$ 8-Br | H | NMR(400MHz, $CDCl_3$) δ ppm: 0.90(3H, t, J=7.3Hz), 1.78–1.84(2H, m), 3.79(3H, s), 4.06(1H, d, J=2.9Hz), 4.11–4.18(1H, m), 4.35(1H, d, J=2.9Hz), 4.68(1H, d, J=14.7Hz), 4.70(1H, d, J=13.2Hz), 4.74(1H, d, J=14.7 Hz), 4.86(1H, d, J=13.2Hz), 4.89(1H, d, J=2.9Hz), 6.65(1H, s), 6.90(1H, s), 7.15–7.55(4H, m) |
| 66-A | $C_2H_5$ | H | 7-$OC_2H_5$ | $CH_3$ | NMR(400MHz, $CDCl_3$) δ ppm: 0.90(3H, t, J=7.3Hz), 1.40(3H, t, J=7.3Hz), 1.56(3H, d, J=6.6Hz), 1.77(2H, dq, J=7.3, 7.3Hz), 3.79(1H, d, J=3.7Hz), 4.02(2H, q, J= 7.3), 4.13(1H, dt, J=3.7, 7.3Hz), 4.32(1H, d, J=2.9 Hz), 4.59(1H, d, J=12.4Hz), 4.59(1H, q, J=6.6Hz), 4.76(1H, d, J=12.4Hz), 4.85(1H, d, J=2.9Hz), 6.68 (1H, d, J=2.9Hz), 6.83(1H, dd, J=2.9, 8.8Hz), 7.2–7.5 (6H, m) |

FORMULATION EXAMPLES OF AND TEST EXAMPLES

Formulation Examples for herbicides of the present invention and Test Examples for herbicidal activity of the formulations are given as follows:

Formulation Example 1: (Wettable powder)

20 Parts by weight of the compound (1) of the present invention, 2 parts by weight of Neopelex (a trade name; Kao Corporation; sodium dodecylbenzene sulfonate), 1 part by weight of Noigen EA80 (a trade name; Daiichi Kogyo Seiyaku, polyoxyethylenenonylphenyl ether), 10 parts by weight of white carbon and 67 parts by volume of diatomaceous earth were thoroughly mashed and blended to prepare a wettable powder.

Formulation Example 2: (Wettable powder)

20 Parts by weight of the compound (6) of the present invention, 2 parts by weight of sodium alkylbenzene sulfonate, 1 part by weight of polyoxyethylenealkylphenyl ether, 10 parts by weight of white carbon black and 67 parts by volume of ziegrite were thoroughly mashed and blended to prepare a wettable powder.

Formulation Example 3: (Wettable powder)

50 Parts by weight of the compound (9) of the present invention, 30 parts by weight of white carbon, 6 parts by weight of polyoxyethylenealkylphenyl ether ammonium sulfate, 2 parts by weight of lignin sodium sulfonate, 12 parts by weight of diatomaceous earth were thoroughly mashed and blended to prepare a wettable powder.

Formulation Example 4: (Flowable agent)

A mixture of 5 parts by weight of the compound (8) of the present invention, 2 parts by weight of lignin sodium sulfonate and 1 part by weight of polyoxyethylenealkylaryl ether were mixed and mashed with 91.7 parts by weight of water into a fine powder using a sand grinder to prepare a flowable agent with the addition of 0.3 parts by weight of Kelzan S (a trade name; Kelco; xanthan gum).

Formulation Example 5: (Flowable agent)

30 Parts by weight of the compound (5) of the present invention and 10 parts by weight of San Ekisu P252 (a trade name; Sanyo-Kokusaku Pulp; lignin sodium sulfonate) dissolved in 50 parts by weight of water were mashed and mixed and then 0.2 part by weight of Kelzan S (a trade name; Kelco; xanthan gum) and 0.2 part by weight of Deltop (a trade name; Takeda Chem. Ind.; an organic iodine antifungal agent) dissolved in 9.6 parts by weight of water were added therein and mixed to prepare a flowable agent.

Formulation Example 6: (powder)

1 Part by weight of the compound (4) of the present invention, 0.5 part by weight of Emulgen 910 (a trade name; Kao Corporation; polyoxyethylenenonylphenyl ether) and 98.5 parts by weight of kaolin clay were thoroughly mashed and mixed to obtain a powder.

Formulation Example 7: (powder)

3 Parts by weight of the compound (5) of the present invention, 3 parts by weight of lignin sodium sulfonate, 2 parts by weight of polyoxyethylenealkylaryl ether and 92 parts by weight of clay were mixed and mashed to prepare a powder.

Formulation Example 8: (Water Dispersible Granule)

55 Parts by weight of the compound (7) of the present invention, 5 parts by weight of Toxanon 60PN, 5 parts by weight of polyoxyethylenealkylaryl ether and 35 parts by weight of white carbon black were thoroughly mixed and then the mixture was moistened with an appropriate amount of water and then compressed to granules using a side-extrusion granulator. The granules were dried at 30°–60° C., broken up and then finely granulated to a diameter of 0.3–0.5 mm using a refiner to obtain a water dispersible granule.

Formulation Example 9: (granule)

3 Parts by weight of the compound (1) of the present invention, 2 parts by weight of Neopelex (a trade name; loc. cit.), 2 parts by weight of SANX (a trade name; Sanyo-Kokusaku Pulp; lignin sodium sulfonate), 70.0 parts by weight of bentonite and 23 parts by weight of talc were thoroughly mixed and moistened with an appropriate amount of water and then granulated using a side-extrusion granulator. The resultant granules were dried in air at 30°–60° C., broken up and then finely granulated using a refiner to a diameter of 0.3–1 mm to obtain a granule.

Formulation Example 10: (granule)

0.5 Part by weight of the compound (4) of the present invention, 2 parts by weight of Gosenol GL-05s (a trade name; Nippon Gosei Kagaku; PVA), 2 parts by weight of San Ekisu P252 (a trade name; Sanyo-Kokusaku Pulp; lignin sodium sulfonate) and 95.5 parts by weight of clay were thoroughly mixed and moistened with an appropriate amount of water. The mixture was then granulated using a side-extrusion granulator. The resultant granules were dried in air at 60°–90° C., broken up and then finely granulated using a refiner to a diameter of 0.3–1 mm to obtain a granule.

Formulation Example 11 (emulsion)

10 Parts by weight of the compound (3) of the present invention, 10 parts by weight of Sorpol 800A (a trade name; Toho Pharmaceutical Inc.; a mixture of non-ionic surfactant and anion surfactant) and 80 parts by weight of o-xylene were mixed and dissolved to obtain an emulsion.

Formulation Example 12: (wettable powder)

20 Parts by weight of the compound (38-A) of the present invention, 2 parts by weight of sodium alkylbenzene sulfonate, 1 part by weight of polyoxyethylenealkylphenyl ether, 15 parts by weight of white carbon and 62 parts by weight of Sieglite are thoroughly mashed and mixed to prepare a wettable powder.

Formulation Example 13: (wettable powder)

50 Parts by weight of the compound (31-A) of the present invention, 30 parts by weight of white carbon, 6 parts by weight of polyoxyethylenealkylphenyl ether ammonium sulfate, 2 parts by weight of lignin sodium sulfonate, 12 parts by weight of diatomaceous earth were thoroughly mashed and mixed to prepare a wettable powder.

Formulation Example 14 (oil-in-water type emulsion EW)

5 Parts by weight of the compound (48-A) of the present invention, 4 parts by weight of Toxanon FW-10 (a trade name; Sanyo Kasei Kogyo; polymer anion), 0.3 part by weight of xanthan gum, 0.2 part by weight of Deltop and 2 parts by weight of polyoxyethylenealkylaryl ether were emulsified with 88.5 parts by weight of water by a homomixer to obtain an oil-in-water type emulsion EW.

Formulation Example 15 (oil-in-water type emulsion EW)

30 Parts by weight of the compound (49-A) of the present invention, 4 parts by weight of Gosenol KH-20 (a trade name; Nippon Gosei Kagaku; a protective colloid forming agent), 0.3 part by weight of xanthan gum, 0.2 part by weight of Deltop (a trade name; Takeda Pharmaceutical Inc.; organic iodine antifungal agent) and 4 parts by weight of polyoxyethylenealkylaryl ether were mashed and mixed with 61.5 parts by weight of water to obtain an oil-in-water type emulsion EW.

Formulation Example 16 (Water Dispersible Granular)

50 Parts by weight of the compound (47) of the present invention, 5 parts by weight of Toxanon 60PN, 5 parts by weight of polyoxyethylenealkylaryl ether and 40 parts by weight of white carbon were thoroughly mixed and then moistened with an appropriate amount of water. The mixture was compressed to granules using a side-extrusion granulator. The resultant granules were dried at 30°–60° C., broken up and then finely granulated using a refiner to a diameter of 0.3–1 mm using a refiner to obtain a water dispersible granule.

Formulation Example 17: (granule)

3.0 Parts by weight of the compound of the present invention (37-A), 2 parts by weight of Neopelex (a trade name; loc. cit.), 2 parts by weight of San Ekisu P252 (a trade name; Sanyo-Kokusaku Pulp; lignin sodium sulfonate), 70.0 parts by weight of bentonite and 23 parts by weight of talc were thoroughly mixed and moistened with an appropriate amount of water and the mixture was then granulated using a side-extrusion granulator. The resultant granules were dried in air at 30°–60° C., broken up and then finely granulated using a refiner to a diameter of 0.3–1 mm to obtain a granule.

Formulation Example 18: (granule)

1.0 Part by weight of the compound of the present invention (44-A), 2 parts by weight of Gosenol GL-05s (Nippon Gosei Kagaku; PVA), 2 parts by weight of San Ekisu P252 (Sanyo-Kokusaku Pulp; lignin sodium sulfonate) and 95.0 parts by weight of clay were thoroughly mixed and moistened with an appropriate amount of water and the mixture was then granulated using a side-extrusion granulator. The resultant granules were dried in air at 30°–90° C., broken up and then finely granulated using refiner to a diameter of 0.3–1 mm to obtain a granular.

Test Example 1: Flooding soil treatment test (pre-emergence of weeds)

1/5000-are Wagner pots were filled with soil, seeded with *Echinochloa oryzicola, Monochoria vaginalis, Scirpus juncoides* and *Lindernia pyxidaria* and then flooded with water. Two plants of paddy rice (with 2–3 leaves, two seedlings per plant) were transplanted to these pots and were grown in a green house. One day after the transplant (preemergence of weeds), the pots were treated with granules (which were prepared according to the method described in the abovementioned Formulation Example 9), containing test compounds of 3 kg/ha. Thirty days after the treatment, the degree of weed control and damage by the chemicals on the rice plants were investigated. Results are shown in Table 4.

In the Table, the degree of weed control and damage by herbicides on crop plants are denoted as follows by comparing the growth rates of treated plants with those of corresponding untreated plants (growth rate is expressed as a ratio (percent) of the air dry weight of treated plant to that of untreated plant).

| Degree | Growth rate (%) | Extent of damage |
|--------|-----------------|------------------|
| 5 | 0–5 | Dead |
| 4 | 6–10 | Sever damages |
| 3 | 11–40 | Medium damages |
| 2 | 41–70 | Small damages |
| 1 | 71–90 | Slight damages |
| 0 | 91–100 | None |

TABLE 4

Results of flooding soil treatment tests (pre-emergence of weeds)

| Compound No. | Echinochloa oryzicola | Monochoria vaginalis | Scirpus juncoides | Lindernia pyxidaria | Paddy rice |
|---|---|---|---|---|---|
| 1 | 5 | 5 | 5 | 5 | 0 |
| 2 | 5 | 5 | 5 | 5 | 0 |
| 3 | 5 | 5 | 5 | 5 | 0 |
| 4 | 5 | 5 | 5 | 5 | 0 |
| 5 | 5 | 5 | 5 | 5 | 0 |
| 6 | 5 | 5 | 5 | 5 | 0 |
| 7 | 5 | 5 | 5 | 5 | 0 |
| 8 | 5 | 5 | 5 | 5 | 0 |
| 9 | 5 | 5 | 5 | 5 | 0 |
| 10 | 5 | 5 | 5 | 5 | 0 |
| 11 | 5 | 5 | 5 | 5 | 0 |
| 12 | 5 | 5 | 5 | 5 | 0 |
| 13 | 5 | 5 | 5 | 5 | 0 |
| 14 | 5 | 5 | 5 | 5 | 0 |
| 15 | 5 | 5 | 5 | 5 | 0 |
| 17 | 5 | 5 | 5 | 5 | 0 |
| 21 | 5 | 5 | 5 | 5 | 0 |
| 25 | 5 | 5 | 5 | 5 | 0 |
| 26 | 5 | 5 | 5 | 5 | 0 |
| 27 | 5 | 5 | 5 | 5 | 0 |
| 30 | 5 | 5 | 5 | 5 | 0 |
| 34 | 5 | 5 | 5 | 5 | 0 |
| 35 | 5 | 5 | 5 | 5 | 0 |
| 36 | 5 | 5 | 5 | 5 | 0 |
| 43 | 5 | 5 | 5 | 5 | 0 |
| 52 | 5 | 5 | 5 | 5 | 0 |
| 55 | 5 | 5 | 5 | 5 | 0 |
| 57 | 5 | 5 | 5 | 5 | 0 |
| 59 | 5 | 5 | 5 | 5 | 0 |
| 60 | 5 | 5 | 5 | 5 | 0 |
| 61 | 5 | 5 | 5 | 5 | 0 |
| 62 | 5 | 5 | 5 | 5 | 0 |
| 63 | 5 | 5 | 5 | 5 | 0 |
| 64 | 5 | 5 | 5 | 5 | 0 |

TABLE 4-continued

Results of flooding soil treatment tests (pre-emergence of weeds)

| Compound No. | Echinochloa oryzicola | Monochoria vaginalis | Scirpus juncoides | Lindernia pyxidaria | Paddy rice |
|---|---|---|---|---|---|
| 65 | 5 | 5 | 5 | 5 | 0 |
| 66-A | 5 | 5 | 5 | 5 | 0 |
| 67-A | 5 | 5 | 5 | 5 | 0 |
| 68-A | 5 | 5 | 5 | 5 | 0 |
| 68-B | 5 | 5 | 5 | 5 | 0 |

Test Example 2 Flooding soil treatment test (post emergence of weeds)

1/5000-are Wagner pots were filled with soil, seeded with *Echinochloa oryzicola, Monochoria vaginalis, Scirpus juncoides* and *Lindernia pyxidaria* and then flooded with water. Two plants of paddy rice (with 2–3 leaves, two seedlings per plant) were transplanted to these pots and were grown in a green house. At the 2nd leaf stage of *Echinochloa oryzicola*, the pots were treated with granules (which were prepared according to the method described in the above-mentioned Formulation Example 9), containing test compounds of 3 kg/ha. Thirty days after the treatment, the degree of weed control and damage by the chemicals on the rice plants were investigated. Results are shown in Table 5.

In the Table, the degree of weed control and damage by herbicides on crop plants are denoted in the same manner as described in Test Example 1.

TABLE 5

Results of flooding soil treatment tests (post emergence of weeds)

| Compound No. | Echinochloa oryzicola | Monochoria vaginalis | Scirpus juncoides | Lindernia pyxidaria | Paddy rice |
|---|---|---|---|---|---|
| 1 | 5 | 5 | 5 | 5 | 0 |
| 2 | 5 | 5 | 5 | 5 | 0 |
| 3 | 5 | 5 | 5 | 5 | 0 |
| 4 | 5 | 5 | 5 | 5 | 0 |
| 5 | 5 | 5 | 5 | 5 | 0 |
| 6 | 5 | 5 | 5 | 5 | 0 |
| 7 | 5 | 5 | 5 | 5 | 0 |
| 8 | 5 | 5 | 5 | 5 | 0 |
| 9 | 5 | 5 | 5 | 5 | 0 |
| 10 | 5 | 5 | 5 | 5 | 0 |
| 11 | 5 | 5 | 5 | 5 | 0 |
| 12 | 5 | 5 | 5 | 5 | 0 |
| 13 | 5 | 5 | 5 | 5 | 0 |
| 14 | 5 | 5 | 5 | 5 | 0 |
| 15 | 5 | 5 | 5 | 5 | 0 |
| 16 | 5 | 5 | 5 | 5 | 0 |
| 17 | 5 | 5 | 5 | 5 | 0 |
| 18 | 5 | 5 | 5 | 5 | 0 |
| 19 | 5 | 5 | 5 | 5 | 0 |
| 20 | 5 | 5 | 5 | 5 | 0 |
| 21 | 5 | 5 | 5 | 5 | 0 |
| 22-A | 5 | 5 | 5 | 5 | 0 |
| 23-A | 5 | 5 | 5 | 5 | 0 |
| 23-B | 5 | 5 | 5 | 5 | 0 |
| 24-A | 5 | 5 | 5 | 5 | 0 |
| 24-B | 5 | 5 | 5 | 5 | 0 |
| 25 | 5 | 5 | 5 | 5 | 0 |
| 26 | 5 | 5 | 5 | 5 | 0 |
| 27 | 5 | 5 | 5 | 5 | 0 |
| 28 | 5 | 5 | 5 | 5 | 0 |
| 29 | 5 | 5 | 5 | 5 | 0 |
| 30 | 5 | 5 | 5 | 5 | 0 |
| 31-A | 5 | 5 | 5 | 5 | 0 |
| 32-B | 5 | 5 | 5 | 5 | 0 |
| 33-A | 5 | 5 | 5 | 5 | 0 |
| 33-B | 5 | 5 | 5 | 5 | 0 |
| 34 | 5 | 5 | 5 | 5 | 0 |
| 35 | 5 | 5 | 5 | 5 | 0 |
| 36 | 5 | 5 | 5 | 5 | 0 |
| 37-A | 5 | 5 | 5 | 5 | 0 |
| 37-B | 5 | 5 | 5 | 5 | 0 |
| 38-A | 5 | 5 | 5 | 5 | 0 |
| 38-B | 5 | 5 | 5 | 5 | 0 |
| 39-A | 5 | 5 | 5 | 5 | 0 |
| 39-B | 5 | 5 | 5 | 5 | 0 |
| 40-A | 5 | 5 | 5 | 5 | 0 |
| 40-B | 5 | 5 | 5 | 5 | 0 |
| 41-A | 5 | 5 | 5 | 5 | 0 |
| 42 | 5 | 5 | 5 | 5 | 0 |
| 43 | 5 | 5 | 5 | 5 | 0 |
| 44-A | 5 | 5 | 5 | 5 | 0 |
| 44-B | 5 | 5 | 5 | 5 | 0 |
| 45-A | 5 | 5 | 5 | 5 | 0 |
| 46-A | 5 | 5 | 5 | 5 | 0 |
| 46-B | 5 | 5 | 5 | 5 | 0 |
| 47 | 5 | 5 | 5 | 5 | 0 |
| 48-A | 5 | 5 | 5 | 5 | 0 |
| 49-A | 5 | 5 | 5 | 5 | 0 |
| 50-B | 5 | 5 | 5 | 5 | 0 |
| 50-A | 5 | 5 | 5 | 5 | 0 |
| 51-B | 5 | 5 | 5 | 5 | 0 |
| 51 | 5 | 5 | 5 | 5 | 0 |
| 52 | 5 | 5 | 5 | 5 | 0 |
| 53 | 5 | 5 | 5 | 5 | 0 |
| 54 | 5 | 5 | 5 | 5 | 0 |
| 55 | 5 | 5 | 5 | 5 | 0 |
| 56 | 5 | 5 | 5 | 5 | 0 |
| 57 | 5 | 5 | 5 | 5 | 0 |
| 58 | 5 | 5 | 5 | 5 | 0 |
| 59 | 5 | 5 | 5 | 5 | 0 |
| 60 | 5 | 5 | 5 | 5 | 0 |
| 66-A | 5 | 5 | 5 | 5 | 0 |
| 67-A | 5 | 5 | 5 | 5 | 0 |
| 68-A | 5 | 5 | 5 | 5 | 0 |
| 68-B | 5 | 5 | 5 | 5 | 0 |

Test Example 3 Upland soil treatment test (pre-emergence of weeds)

1/2500-are resin pots were filled with soil, covered with soil mixed with seeds of *Echinochloa sp., Digitaria adscendeus, Setaria viridis, Stellaria media, Amaranthus retroflexus,* soybeans and cotton to a depth of 1–2 cm and then placed in a green house. One day after seeding (pre-emergence of weeds), specified amounts of the wettable powders (which were prepared according to the method described in the above-mentioned Formulation Example 1) which were diluted with water to contain test compounds at a concentration of 3 kg/ha were evenly sprayed on the surface of the soil using a pressure microspray in an amount corresponding to 10 liters/are. Thirty days after spraying, the degree of weed control and damage by the chemicals on the crops were investigated. Results are shown in Table 6. In the Fable, the degree of weed control and damage by herbicides on crop plants are denoted in the same manner as described in Test Example 1.

TABLE 6

Results of upland soil treatment test (pre-emergence of weeds)

| Compound No. | E. sp. | DA | SV | SM | AR | Soybeans | Cotton |
|---|---|---|---|---|---|---|---|
| 1 | 5 | 5 | 5 | 5 | 5 | 0 | 0 |
| 2 | 5 | 5 | 5 | 5 | 5 | 0 | 0 |
| 3 | 5 | 5 | 5 | 5 | 5 | 0 | 0 |
| 5 | 5 | 5 | 5 | 5 | 5 | 0 | 0 |
| 6 | 5 | 5 | 5 | 5 | 5 | 0 | 0 |
| 7 | 5 | 5 | 5 | 5 | 5 | 0 | 0 |
| 8 | 5 | 5 | 5 | 5 | 5 | 0 | 0 |
| 9 | 5 | 5 | 5 | 5 | 5 | 0 | 0 |
| 11 | 5 | 5 | 5 | 5 | 5 | 0 | 0 |
| 12 | 5 | 5 | 5 | 5 | 5 | 0 | 0 |
| 16 | 5 | 5 | 5 | 5 | 5 | 0 | 0 |
| 18 | 5 | 5 | 5 | 5 | 5 | 0 | 0 |
| 19 | 5 | 5 | 5 | 5 | 5 | 0 | 0 |
| 20 | 5 | 5 | 5 | 5 | 5 | 0 | 0 |
| 22-A | 5 | 5 | 5 | 5 | 5 | 0 | 0 |
| 23-A | 5 | 5 | 5 | 5 | 5 | 0 | 0 |
| 23-B | 5 | 5 | 5 | 5 | 5 | 0 | 0 |
| 24-A | 5 | 5 | 5 | 5 | 5 | 0 | 0 |
| 24-B | 5 | 5 | 5 | 5 | 5 | 0 | 0 |
| 28 | 5 | 5 | 5 | 5 | 5 | 0 | 0 |
| 31-A | 5 | 5 | 5 | 5 | 5 | 0 | 0 |
| 40-A | 5 | 5 | 5 | 5 | 5 | 0 | 0 |
| 40-B | 5 | 5 | 5 | 5 | 5 | 0 | 0 |
| 41-A | 5 | 5 | 5 | 5 | 5 | 0 | 0 |
| 48-A | 5 | 5 | 5 | 5 | 5 | 0 | 0 |
| 51 | 5 | 5 | 5 | 5 | 5 | 0 | 0 |
| 53 | 5 | 5 | 5 | 5 | 5 | 0 | 0 |
| 54 | 5 | 5 | 5 | 5 | 5 | 0 | 0 |
| 56 | 5 | 5 | 5 | 5 | 5 | 0 | 0 |
| 58 | 5 | 5 | 5 | 5 | 5 | 0 | 0 |

E. sp. = Echinochloa sp. DA = *Digitaria adscendeus* SV = *Setaria viridis* SM = *Stellaria media* AR = *Amaranthus retroflexus*

Test Example 4: Foliar application on upland plants (post emergence of weeds)

1/10000-are resin pots were filled with soil, seeded with Echinochloa sp., *Digitaria adscendeus, Setaria viridis, Stellaria media, Amaranthus retroflexus*, soybeans and cotton and then placed in a green house. When 2–3 leaves of each plant appeared, specified amounts of the wettable powders (which were prepared according to the method described in the above-mentioned Formulation Example 2), which were diluted with water to contain test compounds at a concentration of 3 kg/ha, were evenly sprayed over the head of plants using a pressure microspray in an amount corresponding to 10 liters/are. Thirty days after spraying, the degree of weed control and damage by the chemicals on the crops were investigated. Results are shown in Table 7. In the Table, the degree of weed control and damage by herbicides on the crop plants are denoted in the same manner as described in Test Example 1.

TABLE 7

Results of foliar application on upland plants (post emergence of weeds)

| Compound No. | E. sp. | DA | SV | SM | AR | Soybeans | Cotton |
|---|---|---|---|---|---|---|---|
| 1 | 5 | 5 | 5 | 65 | 5 | 0 | 0 |
| 2 | 5 | 5 | 5 | 5 | 5 | 0 | 0 |
| 3 | 5 | 5 | 5 | 5 | 5 | 0 | 0 |
| 4 | 5 | 5 | 5 | 5 | 5 | 0 | 0 |
| 6 | 5 | 5 | 5 | 5 | 5 | 0 | 0 |
| 8 | 5 | 5 | 5 | 5 | 5 | 0 | 0 |
| 9 | 5 | 5 | 5 | 5 | 5 | 0 | 0 |
| 10 | 5 | 5 | 5 | 5 | 5 | 0 | 0 |
| 13 | 5 | 5 | 5 | 5 | 5 | 0 | 0 |
| 14 | 5 | 5 | 5 | 5 | 5 | 0 | 0 |
| 29 | 5 | 5 | 5 | 5 | 5 | 0 | 0 |
| 39-A | 5 | 5 | 5 | 5 | 5 | 0 | 0 |
| 39-B | 5 | 5 | 5 | 5 | 5 | 0 | 0 |
| 42 | 5 | 5 | 5 | 5 | 5 | 0 | 0 |
| 45-A | 5 | 5 | 5 | 5 | 5 | 0 | 0 |
| 46-A | 5 | 5 | 5 | 5 | 5 | 0 | 0 |
| 46-B | 5 | 5 | 5 | 5 | 5 | 0 | 0 |
| 47 | 5 | 5 | 5 | 5 | 0 | 0 | 0 |
| 50-A | 5 | 5 | 5 | 5 | 5 | 0 | 0 |
| 50-B | 5 | 5 | 5 | 5 | 5 | 0 | 0 |

E. sp. = Echinochloa sp. DA = *Digitaria adscendeus* SV = *Setaria viridis* SM = *Stellaria media* AR = *Amaranthus retroflexus*

Test Example 5: flooding soil treatment test (post emergence of weeds)

1/500-are Wagner pots were filled with soil, seeded with *Echinochloa oryzicola* and then flooded with water. Two plants of paddy rice (2–3 leaves, two seedlings per plank) were transplanted to these pots and were grown in a green house. At the 2nd leaf stage of *Echinochloa oryzicola*, the pots were treated with specified amounts of granules (which were prepared according to the method described in the above-mentioned Formulation Example 9) to make concentrations of test compounds an 1.0, 0.5 and 0.2 kg/ha. Thirty days after the treatment, tile degree of weed control and damage by the chemicals on the paddy rice were investigated. Results are shown in Table 8.

in the Table, the degree of weed control and damage by herbicides on crop plants are denoted in the same manner as described in Test Example 1.

TABLE 8

Results of flooding soil treatment test (post emergence of weeds)

| Compound No. | Echinochloa oryzicola | | | Paddy rice |
|---|---|---|---|---|
| | 1 kg/ha | 0.5 kg/ha | 0.2 kg/ha | 1 kg/ha |
| 8-A | 5 | 5 | 5 | 0 |
| 8-B | 5 | 5 | 4 | 0 |
| 33-A | 5 | 5 | 5 | 0 |
| 33-B | 5 | 5 | 4 | 0 |
| 37-A | 5 | 5 | 5 | 0 |
| 37-B | 5 | 5 | 4 | 0 |
| 38-A | 5 | 5 | 5 | 0 |
| 38-B | 5 | 5 | 4 | 0 |
| 40-A | 5 | 5 | 5 | 0 |
| 40-B | 5 | 4 | 4 | 0 |
| 44-A | 5 | 5 | 5 | 0 |
| 44-B | 5 | 5 | 4 | 0 |
| 49-A | 5 | 5 | 5 | 0 |
| 49-B | 5 | 5 | 4 | 0 |

What is claimed is:

1. Substituted tetrahydrofuran derivative of the general formula (II):

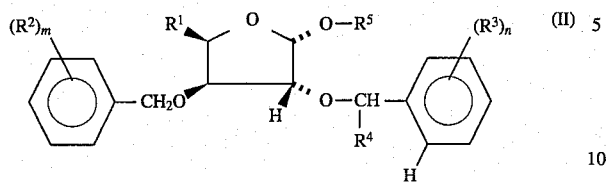

in which $R^1$ is a lower alkyl group, $R^2$ is a lower alkyl group, lower alkoxy group, halogen atom or lower alkyl group substituted by a halogen atom, $R^3$ is a lower alkyl group, lower alkoxy group, halogen atom, lower alkyl group substituted by a halogen atom, phenoxy group or benzyloxy group, $R^4$ is a hydrogen atom or lower alkyl group, m and n are any integers between 0 and 4, each $R^2$ may be different when m is 2–4, each $R^3$ may be different when n is 2–4, and $R^5$ is a lower alkyl group or lower acyl group.

2. Substituted tetrahydrofuran derivative in claim 1, in which $R^1$ is a methyl or ethyl group, $R^2$ is an alkyl group having 1 to 4 carbon atoms, or a halogen atom, $R^3$ is an alkyl group having 1 to 4 carbon atoms, an alkoxy group having 1 to 4 carbon atoms, or a halogen atom, $R^4$ is a hydrogen atom, or a methyl or ethyl group, $R^5$ is an alkyl group having 1 to 4 carbon atoms or an acyl group having 1 to 4 carbon atoms, m and n are any integers between 0 and 2 and each $R^2$ may be different when m is 2 and each $R^3$ may be different when n is 2.

3. Substituted tetrahydrofuran derivative in claim 2, in which $R^1$ is a methyl or ethyl group, $R^2$ is a methyl group or a fluorine or chlorine atom, $R^3$ is a methyl, methoxy or ethoxy group, or a fluorine or chlorine atom, $R^4$ is a hydrogen atom, or a methyl or ethyl group, $R^5$ is a methyl group or an acetyl group, m and n are any integers between 0 and 2 and each $R^2$ may be different when m is 2 and each $R^3$ may be different when n is 2.

* * * * *